(12) United States Patent  
Ikawa et al.

(10) Patent No.: US 8,871,146 B2  
(45) Date of Patent: Oct. 28, 2014

(54) STERILIZATION METHOD AND APPARATUS

(76) Inventors: Satoshi Ikawa, Sakai (JP); Katsuhisa Kitano, Ibaraki (JP); Satoshi Hamaguchi, Kyoto (JP)

( * ) Notice: Subject to any disclaimer, the term of this patent is extended or adjusted under 35 U.S.C. 154(b) by 599 days.

(21) Appl. No.: 12/771,088

(22) Filed: Apr. 30, 2010

(65) Prior Publication Data

US 2010/0209293 A1    Aug. 19, 2010

Related U.S. Application Data

(63) Continuation of application No. 12/680,018, filed as application No. PCT/JP2008/002670 on Sep. 25, 2008, now abandoned.

(30) Foreign Application Priority Data

Sep. 27, 2007   (JP) ................................. 2007-251194

(51) Int. Cl.  
*A61L 9/00*    (2006.01)  
*A23L 3/26*    (2006.01)  
(Continued)

(52) U.S. Cl.  
CPC ... *A61L 2/14* (2013.01); *A23L 3/26* (2013.01); *C02F 1/30* (2013.01); *C02F 1/722* (2013.01); *C02F 2305/023* (2013.01); *C02F 1/50* (2013.01); *C02F 2201/3226* (2013.01); *C02F 1/4608* (2013.01)  
USPC .................. 422/29; 422/22; 422/23; 422/28; 205/687; 205/688; 205/701

(58) Field of Classification Search  
CPC ...................................... A61L 2/14

USPC ........... 422/22, 23, 28, 29; 205/687, 688, 701  
See application file for complete search history.

(56) References Cited

U.S. PATENT DOCUMENTS 5,749,895 A    5/1998   Sawyer et al.  
6,149,878 A   11/2000   Jacob et al.  
(Continued)

FOREIGN PATENT DOCUMENTS

JP        3-237979 A   10/1991  
JP     2000-107754 A    4/2000  
(Continued)

OTHER PUBLICATIONS

Supplementary European Search Report dated Aug. 26, 2010, issued in the corresponding European Application No. 08833279.6-2113.

(Continued)

*Primary Examiner* — Regina M Yoo  
(74) *Attorney, Agent, or Firm* — Buchanan Ingersoll & Rooney PC

(57) ABSTRACT

An object of the present invention is to efficiently sterilize microorganisms present in or on a surface of a liquid. Plasma is generated in a vicinity of or in a manner to make contact with a liquid whose pH value is adjusted to become 4.8 or lower, more preferably 4.5 or lower. The plasma is generated in an atmospheric gas containing nitrogen, e.g., in the air. Superoxide anion radicals ($O_2^-$.) that are generated by the plasma react with protons ($H^+$) in the liquid to form hydroperoxy radicals (HOO.). Further, nitrogen and oxygen included in the air are combined together by the action of plasma to form nitrogen oxide such as nitric oxide (NO.). The nitric oxide (NO.) combines with the hydroperoxy radicals (HOO.) to become peroxynitrite ($ONOOH(ONOO^-)$) having a high microbiocidal activity.

7 Claims, 21 Drawing Sheets

(51) Int. Cl.

| | | |
|---|---|---|
| *C02F 1/30* | (2006.01) | |
| *A61L 2/14* | (2006.01) | |
| *C02F 1/50* | (2006.01) | |
| A61L 2/00 | (2006.01) | |
| A61L 2/18 | (2006.01) | |
| A61L 2/02 | (2006.01) | |
| B01D 17/06 | (2006.01) | |
| C02F 1/461 | (2006.01) | |
| C25F 1/00 | (2006.01) | |
| C25F 5/00 | (2006.01) | |
| C25F 7/00 | (2006.01) | |
| C02F 1/72 | (2006.01) | |
| C02F 1/46 | (2006.01) | |

(56) References Cited

U.S. PATENT DOCUMENTS

| | | | |
|---|---|---|---|
| 6,562,386 B2 | 5/2003 | Ruan et al. | |
| 7,011,790 B2* | 3/2006 | Ruan et al. | 422/22 |
| 7,658,155 B2* | 2/2010 | Chapman et al. | 110/346 |
| 2002/0155594 A1* | 10/2002 | Hsieh et al. | 435/299.2 |
| 2003/0026877 A1 | 2/2003 | Ruan et al. | |
| 2003/0180421 A1 | 9/2003 | Ruan et al. | |
| 2004/0022669 A1* | 2/2004 | Ruan et al. | 422/22 |
| 2005/0178330 A1* | 8/2005 | Goodwin et al. | 118/723 E |
| 2006/0023391 A1* | 2/2006 | On | 361/212 |
| 2006/0060464 A1 | 3/2006 | Chang | |
| 2006/0110700 A1 | 5/2006 | Cipolla et al. | |
| 2006/0127271 A1* | 6/2006 | Ruan et al. | 422/22 |
| 2006/0177360 A1* | 8/2006 | On et al. | 422/186.21 |
| 2008/0206717 A1 | 8/2008 | Mylius | |
| 2009/0120797 A1* | 5/2009 | Daigle | 205/85 |

FOREIGN PATENT DOCUMENTS

| | | | | |
|---|---|---|---|---|
| JP | 2004-143519 A | 5/2004 | | |
| JP | 2004-522455 A | 7/2004 | | |
| JP | 2004-290612 A | 10/2004 | | |
| JP | 2005-529455 A | 9/2005 | | |
| WO | WO 02/058449 | 8/2002 | | |
| WO | WO 02/089612 A1 | 11/2002 | | |
| WO | WO 03/011346 | 2/2003 | | |
| WO | WO 03/096767 A1 | 11/2003 | | |
| WO | WO 2005/067984 | 7/2005 | | |
| WO | WO 2006078338 A2 * | 7/2006 | | C23F 4/00 |
| WO | WO 2006/079801 A1 | 8/2006 | | |
| WO | WO 2006/119997 | 11/2006 | | |
| WO | WO 2006/137832 | 12/2006 | | |
| WO | WO 2007000607 A1 * | 1/2007 | | F23G 5/00 |

OTHER PUBLICATIONS

English translation of the International Preliminary Report on Patentability issued in International Application No. PCT/JP2008/002670.

International Search Report of PCT/2008/002670 dated Oct. 28, 2008.

Kaoru Tamazawa, "Features and Problems on the Plasma Sterilization and Future Prospect of the New Sterilization Using Low-Temperature-Plasma", vol. 32, No. 1, pp. 13-30, 2004 (with concise explanation).

Masaaki Nagatsu, "Plasma Sterilization", J. Plasma Fusion Res., vol. 83, No. 7, 2007, pp. 601-606 (with concise explanation).

Official Action issued by European Patent Office on Sep. 11, 2013 in European Application No. 08 833 279.6-1356 (6 pgs).

* cited by examiner

STERILIZATION METHOD AND APPARATUS

CROSS-REFERENCE TO RELATED APPLICATIONS

This application is a continuation of U.S. application Ser. No. 12/680,018 filed on Mar. 25, 2010, which is a U.S. national stage application of International Application No. PCT/JP2008/002670 filed on Sep. 25, 2008 and which claims priority to Japanese Application No. 2007-251194 filed on Sep. 27, 2007, the entire contents of which are incorporated herein by reference.

FIELD

The present invention relates to a sterilization method and a sterilization apparatus using plasma, particularly to a technology to enhance a sterilization capability for sterilizing microorganisms present in a liquid or on a surface thereof by adjusting pH by using an atmospheric pressure plasma as a radicals generating source. The present invention is used for sterilization or complete sterilization of medical equipment, food containers, foods, and other articles; sterilization, complete sterilization, and disinfection of wounds; or a sewage treatment and other various cases requiring a sterilization treatment.

BACKGROUND

Conventionally, the method for sterilizing or completely sterilizing various microorganisms such as bacteria or viruses can be broadly divided into two types, i.e., a physical method (mechanical method) using heat, pressure, or the like, and a chemical method using chemical agents. The physical method includes a high-pressure steam sterilization method (autoclaved sterilization), a gamma sterilization method, an electron beam sterilization method, and the like. The chemical method includes an ethylene oxide gas (EOG) sterilization method, a reduced-pressure hydrogen peroxide plasma sterilization method, and the like.

The physical method is mainly used for complete sterilization of medical equipment. However, since an object to be sterilized is exposed to an extreme physical condition in many cases, the type of object to be sterilized is limited. For example, the autoclave is not applicable to a plastic product that is easily affected by heat, and it is not desirable to sterilize, using gamma rays, materials, precision equipment, or the like that are easily degraded by ultraviolet rays or the like. In addition, a large-scaled apparatus is required in most cases except for using the autoclave, which, in many cases, makes it difficult to choose a place to install the apparatus.

In the case of the chemical method, the chemical agents to be used may exert a harmful influence on the human body. Therefore, a process for securely rendering the agent residue harmless is necessary, which, as a result, requires more cost and time. Particularly, guidance is provided to restrict the use of EOG because it has acute toxicity and a mutagenic property. Especially, when chemical agents are used, complete sterilization in a liquid is difficult. Even if such sterilization is realized, high-concentration chemical agents remain in the liquid as a result. It becomes, then, extremely difficult to detoxify the sterilization agents dissolved in the liquid, i.e., substantially impossible by conventional technologies.

In recent years, on the other hand, investigations for a sterilization method using plasma have been in progress. The plasma is an expression referring to a state of substance in addition to solid, liquid, and gas. Atoms turn into a plasma state consisting of ions and electrons, and acquire a high chemical activity at a high temperature of about 10,000° C. or higher. The plasma is used as a light source represented by a fluorescent lamp or processing used in the semiconductor industry.

Provided as an example of the sterilization method using plasma is the hydrogen peroxide plasma sterilization method (HLPS) as described above. In the HLPS method, a pressure in a chamber is reduced to, for example, as low as 0.3 Torr; hydrogen peroxide is injected and diffused; and high-frequency discharges (10 eV, 13.56 MHz, 400 W) by means of air are performed. Thereafter, clean air is blown into the chamber to bring the pressure therein back to the atmospheric pressure. It is said that, according to the HLPS method, sterilization is performed by radicals (OH.) or the like produced by an oxidation action of hydrogen peroxide and the plasma discharges (Non-patent Document 1: "Features and Problems on the Plasma Sterilization and Future Prospect of the New Sterilization using Low-temperature-plasma", by Kaoru Tamazawa, Bokin Bobai Vol. 32, No. 1, pp. 13~30).

Further, JP-A-2004-290612 discloses a sterilization method which uses hydrogen peroxide as a sterilization chemical agent and combines the same with plasma.

It is also proposed to ignite plasma in a chamber maintained as a vacuum environment after exhausting gas, and sterilize a dried object (Non-patent Document 2: "Plasma Sterilization", by Masaaki Nagatsu, J. Plasma Fusion Res., vol. 83, No. 7 (2007) 601-606). Non-patent Document 2 discloses sterilizing medical equipment such as a knife, a scalpel, and a tube disposed in a non-woven fabric that allows gas to pass therethrough but prevents microorganisms from passing therethrough.

According to the conventional sterilization method utilizing a combination of hydrogen peroxide and plasma, what is currently performed is the sterilization by using hydrogen peroxide that, per se, is a powerful microbiocide, and thereafter the plasma is used to decompose and detoxify the hydrogen peroxide.

In addition to this fact, a pressure vessel is required to use plasma under a vacuum environment in a low pressure. The sterilization is performed only in such a pressure vessel, which casts a lot of restrictions in performing the sterilization.

In recent years, atmospheric pressure plasma has been drawing a lot of attention. The conventional plasma is generated, in often cases, under a low pressure, and it is difficult to use it under an ordinary environment. When the plasma is generated under a high pressure such as an atmospheric pressure, the plasma thus generated tends to become a thermal plasma represented by arc plasma used for arc-welding, because particles that are ionized to become plasma, through frequent collisions with neutral gas particles, reach almost a thermal equilibrium state accompanied by an increase in the temperature of neutral gas component. On the other hand, non-equilibrium plasma is attracting attention. The non-equilibrium plasma is chemically active because it has a sufficiently high electron temperature despite a low neutral gas temperature and formed by creating a non-equilibrium state while ingeniously contriving a way to prevent a thermal relaxation state from being generated. The non-equilibrium plasma is sometimes called low-temperature plasma because the neutral gas temperature is about a room temperature, which is significantly low as compared with the electron temperature.

If such a non-equilibrium plasma can be used for sterilization, the practical value thereof is supposed to be extremely high because restrictions for performing sterilization are largely reduced. However, the technology for effectively sterilizing the microorganisms present in a liquid or on a surface thereof has not been established.

SUMMARY

The present invention is made in light of the problem described above, and it is an object of the present invention to provide a sterilization method and apparatus with which microorganisms present in a liquid or on a surface thereof can be sterilized effectively.

According to one embodiment of the method of the present invention, plasma is generated in a vicinity of or in a manner to make contact with a liquid whose pH value is adjusted to become 4.8 or lower, and radicals generated by the plasma are made contact with the liquid.

In such a case, it is preferable that the plasma be generated in an atmosphere containing nitrogen gas. The plasma may be generated in the air, instead.

It is preferable that the pH value of the liquid be 4.5 or lower, and more preferable that the pH value be 2 or higher but 3.5 or lower.

Superoxide anion radicals ($O_2^-$.) that are generated by the plasma, by making contact with a liquid having a pH value of 4.8 or lower and being diffused in the liquid, react with protons ($H^+$) in the liquid to thereby form hydroperoxy radicals (HOO.). Further, for example, nitrogen and oxygen included in the air are combined together by the action of plasma to thereby form nitrogen oxide such as nitric oxide (NO.) or nitrogen dioxide ($NO_2$.). The nitric oxide (NO.) combines with the hydroperoxy radicals (HOO.) to become peroxynitrite ($ONOOH(ONOO^-)$) having a high microbiocidal activity. A powerful antimicrobial effect is provided by these hydroperoxy radicals (HOO.), peroxynitrite (ONOOH ($ONOO^-$)), and the like.

DESCRIPTION OF EMBODIMENT(S)

Figure 1:
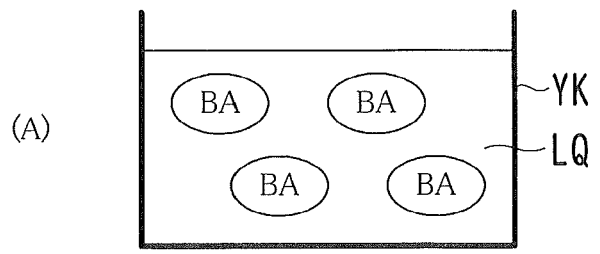
FIG. 1 is a diagram depicting a sterilization method according to the first embodiment of the present invention (a) illustrating how the liquid is prepared by adding the liquid to the container, (b) illustrating how the liquid is adjust to pH of 4.8 or lower, and (c) illustrating how the plasma is generated in the vicinity of a liquid.
Figure 1:
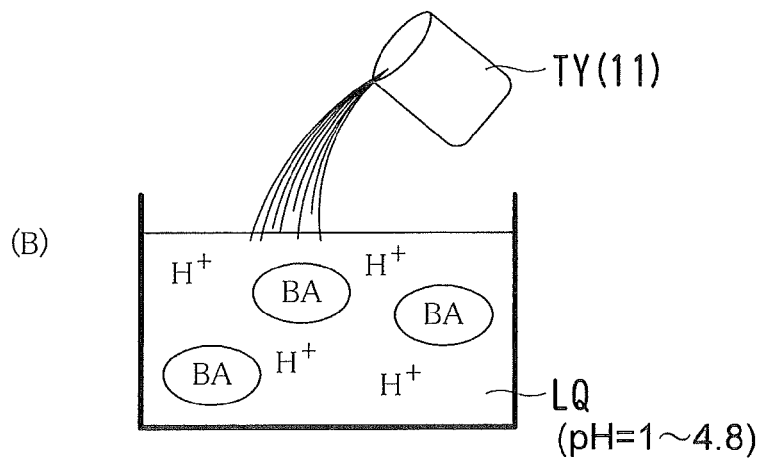
Figure 1:
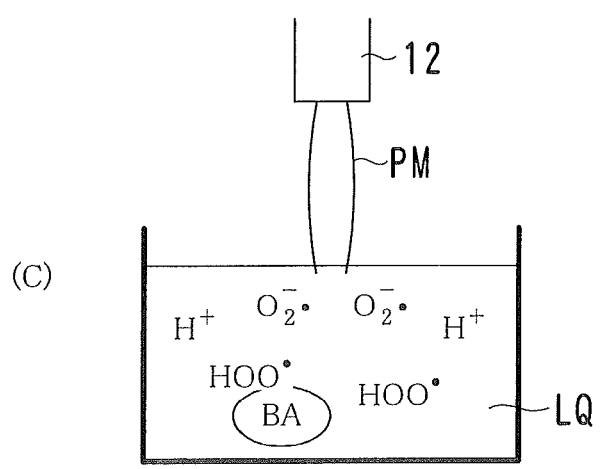

The present invention may be implemented in various embodiments described below.

To be specific, plasma is generated in a vicinity of or in a manner to make contact with a liquid whose pH value is adjusted to become 4.8 or lower, and radicals (free radicals) generated by the plasma are brought into contact with the liquid.

In the case mentioned above, the plasma is generated in an atmosphere containing nitrogen gas. For example, the plasma is generated in the air.

Further, a method for sterilizing microorganisms present in a liquid or on a surface thereof includes a first step of adjusting a pH value of the liquid to 4.8 or lower and a second step of bringing the liquid into contact with plasma following the first step.

A method for sterilizing microorganisms present on a surface of an object or in a vicinity of the surface includes a step of applying a liquid having a pH value of 4.8 or lower to the surface of the object, and a step of exposing the liquid present on the surface of the object to plasma.

Furthermore, a method for sterilizing microorganisms present on a surface of an object or in a vicinity of the surface includes a step of immersing the object in a liquid having a pH value of 4.8 or lower, and a step of exposing the liquid with the object immersed therein to plasma.

A method for sterilizing microorganisms present on a surface of a living body or in a vicinity of the surface includes a step of applying a liquid having a pH value of 4.8 or lower to the surface of the living body, and exposing the liquid present on the surface of the living body to low-temperature plasma.

In the methods described above, the liquid is applied in a form of a gelatin sheet to the surface of the living body.

A sterilization apparatus, for sterilizing microorganisms present in a liquid or on a surface thereof, includes a pH adjustment device that adjusts a pH value of the liquid at 4.8 or lower, and a plasma generation device that emits plasma to the liquid.

A sterilization apparatus, for sterilizing microorganisms present in an object or on a surface thereof, includes a housing capable of surrounding and hermetically enclosing at least a part of the object, a pH adjustment device that supplies a pH adjusting substance such that a pH value of said at least the part of the object becomes 4.8 or lower, a plasma generation device that generates plasma inside the housing, an introduction portion that introduces an atmospheric gas containing nitrogen gas into the housing, and an exhaust portion that draws out the atmospheric gas.

It is preferable that the pH value be adjusted to become 4.5 or lower. It is more preferably that the pH value be adjusted to become 2 or higher but 3.5 or lower.

It should be noted that "complete sterilization" means annihilating or completely inactivating bacteria, fungi, viruses, and the like, and generally requires more strict conditions than in the case of "sterilization". To be specific, the sterilization means a state in which the number of microorganisms is reduced to $1/10^3$ or less of the original microorganisms concentration. However, the complete sterilization means a case in which the survival probability of microorganisms is reduced to $1\times10^{-6}$ or less. To put it differently, in the case of sterilization, although the number of microorganisms is temporarily reduced to a harmless level, the microorganisms may increase in numbers depending on the conditions provided thereafter. On the other hand, since the microorganisms have been entirely annihilated in the case of complete sterilization, the microorganisms will never grow, for example, in retort-packed foods or canned foods unless they are opened.

In the description hereinafter, decreasing the density in number of microorganisms is referred to as "sterilization".

Hereinafter, various embodiments will be described.

[First Embodiment]

As illustrated in FIG. 1(A), preparation is made by feeding a container YK with a liquid LQ, i.e., a target for sterilization. Used as the liquid LQ is water, an aqueous solution, physiological saline, or various other types of liquids. The liquid LQ includes microorganisms such as fungi, bacteria, or viruses, or pathogenetic biological macromolecules such as prions or lipopolysaccharide.

Next, the liquid LQ is adjusted to have a pH value of 4.8 or lower. Preferably, the pH value is adjusted to become 4.5 or lower, or more preferably 3.5 or lower. At the same time, it is also preferable that the pH value be adjusted to be 1 or higher, more preferably 2 or higher to lessen the influence on human body and make the post processing of the liquid LQ easier.

In order to adjust the pH as described above, there are provided such methods as charging acid, or salt that indicates acidity, such as, for example, citric acid ($C_6H_8O_7$) or phosphate (e.g., $KH_2PO_4$) from a charging container TY into the liquid LQ, or blowing a carbonic acid gas ($CO_2$) into the liquid LQ. In this way, when the pH is adjusted and the liquid LQ turns into acidic, protons (hydrogen ions) $H^+$ in the liquid LQ increase as illustrated in FIG. 1(B).

It is to be noted that, although the drawings do not illustrate, such a charging device that charges the acid or salt by means of the charging container TY or a blowing device that blows the carbonic acid gas into the liquid LQ corresponds to a pH adjustment device 11.

Thereafter, the liquid LQ is brought into contact with plasma PM in the air. As a method for bringing the liquid LQ into contact with the plasma PM, FIG. 1(C) illustrates that the surface of the liquid LQ is exposed to a plasma jet that is jetted from a plasma generation device 12. In addition to this method, it is also possible to use a method in which the container YK containing the liquid LQ therein is placed in a plasma environment generated by the plasma generation device. Alternatively, it is also possible to use the plasma generation device having an electrode thereof arranged in the liquid LQ and generate the plasma PM in the liquid LQ. For example, low-temperature plasma is used as the plasma PM.

Figure 2:
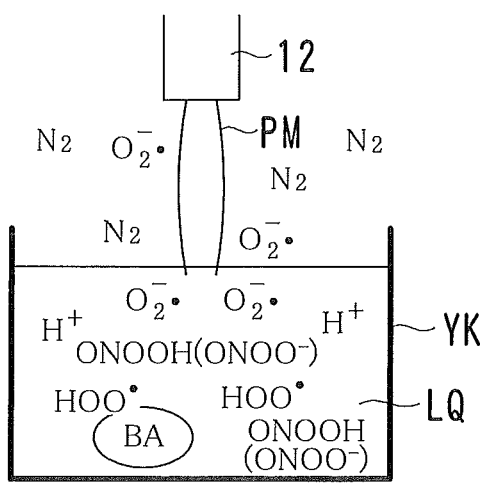
FIG. 2 is a diagram illustrating how the plasma is generated in an atmosphere containing a nitrogen gas.

Alternatively, as illustrated in FIG. 2, it is also possible to generate the plasma PM in an atmosphere containing nitrogen gas, instead of generating the plasma PM in the air.

Although it is not illustrated, it is also possible to generate the plasma PM in an atmosphere containing a mixed gas including nitrogen gas and oxygen gas at an appropriate ratio. Still alternatively, in the case where the oxygen can be obtained from the components of the liquid, for example, when the liquid is water, it is also possible to generate the plasma in an atmosphere containing the nitrogen gas but excluding the oxygen gas. In this case, it is deemed that oxygen radicals are supplied by means of decomposition of the water.

Nitrogen may be fed into the liquid instead of using an atmosphere containing the nitrogen gas to generate the plasma. For example, this is achieved by putting nitric acid or powders of nitrate salt into the liquid and making them dissolve therein. Instead, various substances including nitrogen may be put into the liquid.

It is also possible to generate the plasma PM in the vicinity of the liquid LQ instead of bringing the liquid LQ into contact with the plasma PM.

Active species such as radicals are supplied primarily from a gas phase kept in contact with the plasma, and therefore the plasma is not necessarily brought into contact with the liquid for performing sterilization of the liquid. It is possible to emit the plasma into an atmosphere of air, or a mixed gas containing nitrogen and oxygen to thereby generate radicals in a large amount and supply the radicals thus generated to the target liquid. In this way, it is possible to attain biocidal activities similar to the case where the plasma is made contact with the liquid.

Figure 3:
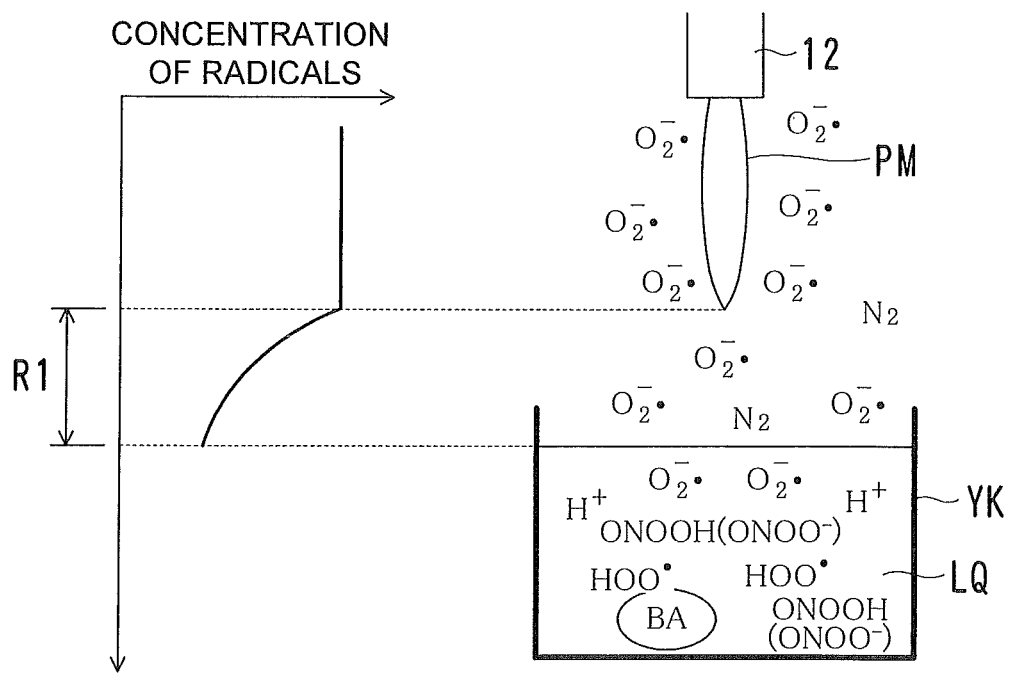
FIG. 3 is a diagram illustrating how the plasma is generated in the vicinity of a liquid.

As illustrated in FIG. 3, the plasma PM may be generated in the vicinity of the liquid LQ In that case, radicals are generated by the plasma PM thus generated, and the generated radicals make contact with the liquid LQ.

As illustrated in FIG. 3, the concentration of the radicals is almost constant in the vicinity of the plasma PM. The farther the position moves from a tip end of the plasma PM, the less the concentration of the radicals becomes. Since the radicals are present within a certain range, such radicals make contact with the liquid LQ. It is preferable that a distance R1 measured from the tip end of the plasma PM to the surface of the liquid LQ be made as small as possible. For example, in the case where a diameter of a jet port of the plasma PM is 4 mm, the distance R1 is about 10 to 20 mm at the maximum.

Figure 4:
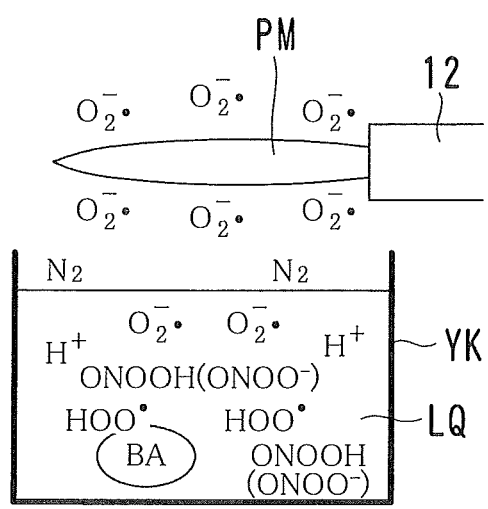
FIG. 4 is a diagram illustrating how the plasma is generated in the vicinity and above a liquid.

The plasma PM may also be generated, as illustrated in FIG. 4, in the upper and vicinity area of the liquid LQ. In this case, the radicals generated by the plasma PM make contact with the liquid LQ.

In this way, it is possible to perform sterilization of the surface of the liquid LQ or in the liquid LQ by generating the plasma PM in the vicinity of or in a manner to make contact with the liquid LQ that is adjusted to have a pH value of 4.8 or lower.

The following is considered to be a principle of the sterilization according to the present embodiment.

Superoxide anion radicals ($O_2^-\cdot$), which are generated by the plasma PM when the plasma PM makes contact with the liquid LQ, diffuse into the liquid LQ. The diffused superoxide anion radicals ($O_2^-\cdot$) react with protons ($H^+$) in the liquid LQ to thereby form hydroperoxy radicals (HOO·).

[Chemical Formula 1]

$$[O_2^-\cdot]+[H^+]\leftrightarrow[HOO\cdot] \tag{1}$$

The right-hand and left-hand sides of the above-mentioned chemical formula are in an equilibrium relationship. The reaction progresses either from the right-hand side to the left-hand side or from the left-hand side to the right-hand side depending on the concentration. The hydroperoxy radicals (HOO.) formed in this way have a powerful antimicrobial effect which sterilize the microorganisms in the liquid LQ.

A value representing the equilibrium constant of this equilibrium reaction (acid dissociation constant), i.e., pKa, is "4.8", which means that the superoxide anion radicals ($O_2^-$.) and the hydroperoxy radicals (HOO.) are present in equal densities when the pH is at 4.8. This also indicates that, in a state in which the pH value is higher than 4.8, the amount of the hydroperoxy radicals (HOO.) reduces extremely, and that, contrary, in a state in which the pH value is lower than 4.8, the amount of the hydroperoxy radicals (HOO.) increases rapidly.

Based on this principle, the pH value of the liquid LQ is adjusted to be 4.8 or lower, and the liquid LQ is made contact with the plasma PM to thereby generate the hydroperoxy radicals (HOO.) with which the microorganisms in the liquid LQ are sterilized. When the pH value of the liquid LQ is adjusted at 4.8 or lower, preferably 4.5 or lower and the liquid LQ is made contact with the plasma PM, it is possible to attain a significantly increased microbiocidal activity.

Hydroxyl radicals (OH.), hydroperoxy radicals (HOO.), superoxide anion radicals ($O_2^-$.), and the like are known as active species having oxidative potential. Sterilization is performed by generating such active species by the plasma that makes contact with the liquid and infiltrating the active species into the liquid. In doing so, it is possible to dramatically enhance the microbiocidal activity by adjusting the pH value of the liquid toward an acidity side, i.e., 4.8 or lower.

The superoxide anion radicals have a relatively long life time but are weak in oxidizability, and are in an equilibrium relationship expressed in Formula (1) with protons ($H^+$) in the liquid. Accordingly, in an acidic environment with a lot of protons ($H^+$), the hydroperoxy radicals (HOO.) having high oxidative potential are prone to be formed. Particularly, at a pH value of 4.8 or lower, which corresponds to the pKa, the ratio of presence of the hydroperoxy radicals (HOO.) increases significantly.

Furthermore, nitrogen and oxygen included in the air are combined together by the action of plasma to thereby form nitrogen oxide, which is a radical of oxygen and nitrogen, such as nitric oxide (NO.) or nitrogen dioxide ($NO_2$.). The nitric oxide (NO.) combines with the hydroperoxy radicals (HOO.) to become peroxynitrite (ONOOH($ONOO^-$)) having a high microbiocidal activity, which, as a result, provides further high microbiocidal activities. It is considered that various active species formed from oxygen and nitrogen generate a synergistic effect to provide a high microbiocidal activity.

[Chemical Formula 2]

$$[OONO_2^-]+[H^+]\leftrightarrow[ONOOH(ONOO^-)] \quad (2)$$

It is deemed that, the microbiocidal activity is attained by the hydroperoxy radicals (HOO.) generated by the liquid LQ having a pH value of 4.8 or lower and the plasma PM, and further the peroxynitrite (ONOOH($ONOO^-$)) is generated because of the presence of nitrogen, which helps attain a further enhanced microbiocidal activity.

Biological materials constituting the microorganisms are altered in properties by the radicals in the liquid, which prevents the microorganisms from further growing or sterilization progresses. This method is applicable to inactivate protein such as pathogenic viruses and prions which are not contained in the microorganisms, and also applicable to chemical modification of biological macromolecules such as protein.

It is possible to generate radicals in the liquid by a chemical method using chemical agents. However, it is also possible to produce radicals in a large amount highly efficiently under a chemically clean environment by using plasma generated mainly with a rare gas. In addition, when the pH value is adjusted at 3.5 or lower, efficient sterilization effect is further secured. When the pH value is adjusted at 2 or higher, the chemical agents used for adjusting the pH do not cause problems, which makes it possible to apply the method to human bodies, odontotherapy, foods, medical equipment, and so on.

Figure 5:
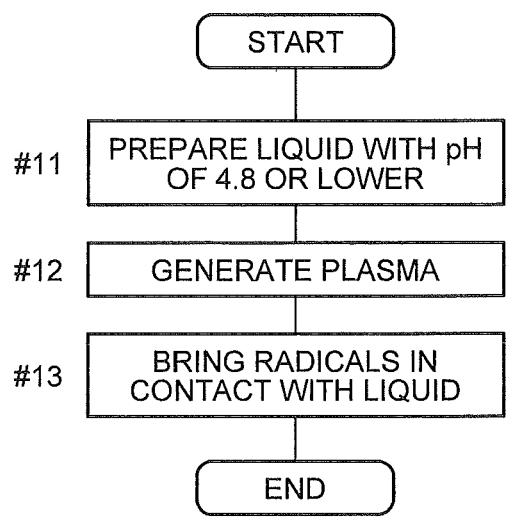
FIG. 5 is a flowchart illustrating a procedure of sterilization method according to the first embodiment.

As illustrated in FIG. 5, according to the sterilization method of the present embodiment, a liquid LQ having a pH value adjusted at 4.8 or lower is prepared (#11), and the liquid LQ is made as a sterilization target as required. Plasma PM is generated in the vicinity of the liquid LQ (#12) to thereby bring radicals into contact with the liquid LQ (#13).

Figure 6:
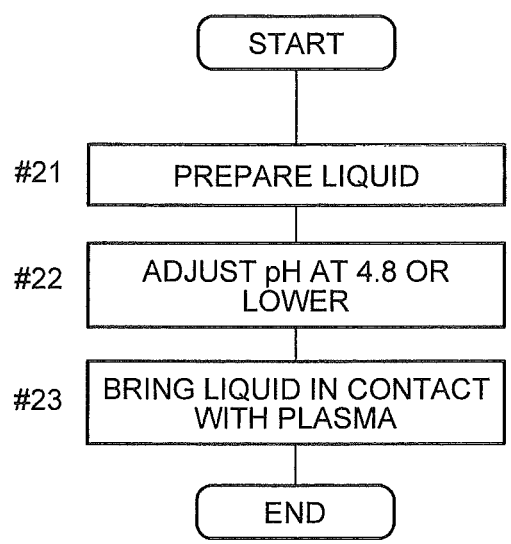
FIG. 6 is a flowchart illustrating another procedure of sterilization method.

As illustrated in FIG. 6, alternatively, a liquid LQ which is a sterilization target is prepared (#21), the liquid LQ is adjusted to have a pH value of 4.8 or lower (#22), and subsequently the liquid LQ is brought into contact with plasma PM (#23).

In this way, according to the present embodiment, active species are produced by making the plasma contact with a surface of the liquid or generating the plasma in the vicinity of the liquid in the air, a nitrogen gas atmosphere, or an atmosphere containing nitrogen gas and oxygen gas. Then, the action of the active species thus produced are strengthened by adjusting the pH in the liquid to thereby effectively perform sterilization of the liquid itself or various articles such as equipment immersed in the liquid.

When the low-temperature plasma is used, it causes less chemical and mechanical damages because the temperature is low and no special chemical agents are required, and does not cause problems by residual gas. This means that it is possible to sterilize, without adverse effects, plastic products and medical equipment having a precision structure such as the one represented by a gastrocamera.

Since the sterilization is performed effectively under two conditions which overlap with each other, i.e., a region with a lowered pH value and a region where radicals produced by the plasma can reach, it becomes possible to perform local sterilization by adjusting each of the regions appropriately. For example, it becomes possible to sterilize a surface layer of wounds of human body.

As described above, in the present embodiment, the charging device for charging acid or salt by means of the charging container TY, or the blowing device that blows the carbonic acid gas into the liquid LQ corresponds to the pH adjustment device 11. The pH adjustment device 11 may also include the container YK, a pH sensor, an adjustment device for adjusting the pH at a predetermined value, and the like. It is also possible to use, as the charging device, a manipulator that, for example, holds and moves the charging container TY, or a spewing device that spews out acid or salt.

Further, the plasma generation device 12 corresponds to the plasma generation device according to the present invention. An entirety including the plasma generation device 12 and the pH adjustment device 11 corresponds to the sterilization apparatus 1 according to the present invention. However, the pH adjustment device 11 and the plasma generation device 12 are not limited to the examples described above, and the pH adjustment device 11 and the plasma generation device having various structures, shapes, or principles may be used.

Next, examples are described hereinafter by incorporating demonstration experiments and the results thereof about the adjustment of pH of the liquid LQ and the case where the liquid is made contact with the plasma PM.

Prior to the description of the examples, a description will be given of a method for evaluating the sterilization.

The evaluation of the number of microorganisms is usually performed by counting the number of colonies formed on the agar plate medium and is expressed in colony forming unit (CFU). The colony is a state in which microbial bodies of a single kind are sufficiently distributed and grown to an extent that can be visible. The CFU is equal to the number of living microorganisms included in an object to be evaluated.

As an index indicating the microbiocidal activity, D value, a time period for the CFU to decrease to $1/10$ of the original value is provided. It is determined that, the smaller the D value is, the greater the microbiocidal l activity is. A sterility assurance level (SAL) indicates a state in which the survival probability of microorganisms is reduced to, as low as $1 \times 10^{-6}$, and the time required to reach the state is referred to as a sterility assurance time. Usually, the initial concentration is assumed to be $1.0 \times 10^6$ CFU/ml, and the time required to reach the SAL is calculated by multiplying the D value by 12. For example, the time required to reach the SAL is 15 minutes in a complete sterilization operation by autoclave at a temperature of 121° C. Such a case indicates that the D value is 75 seconds. In actual cases, since it takes an extra time for the temperature to increase to 121° C. and an extra time for cooling, the entire complete sterilization operation takes about 1 to 1.5 hours.

EXAMPLE 1

In Example 1, the sterilization effects are examined for each of the cases where the liquids having different pH values are exposed to the plasma PM and where they are not exposed.

Specifically, two sets of microbial suspension containing *Escherichia coli* are prepared. Each set is made up of two types of pH values individually adjusted at "6.0" and "3.5". One of the sets is exposed to the plasma PM for two minutes, and the other is not exposed. The result of counting the number of bacteria by a colony counting method is illustrated in FIG. 7.

Figure 7:
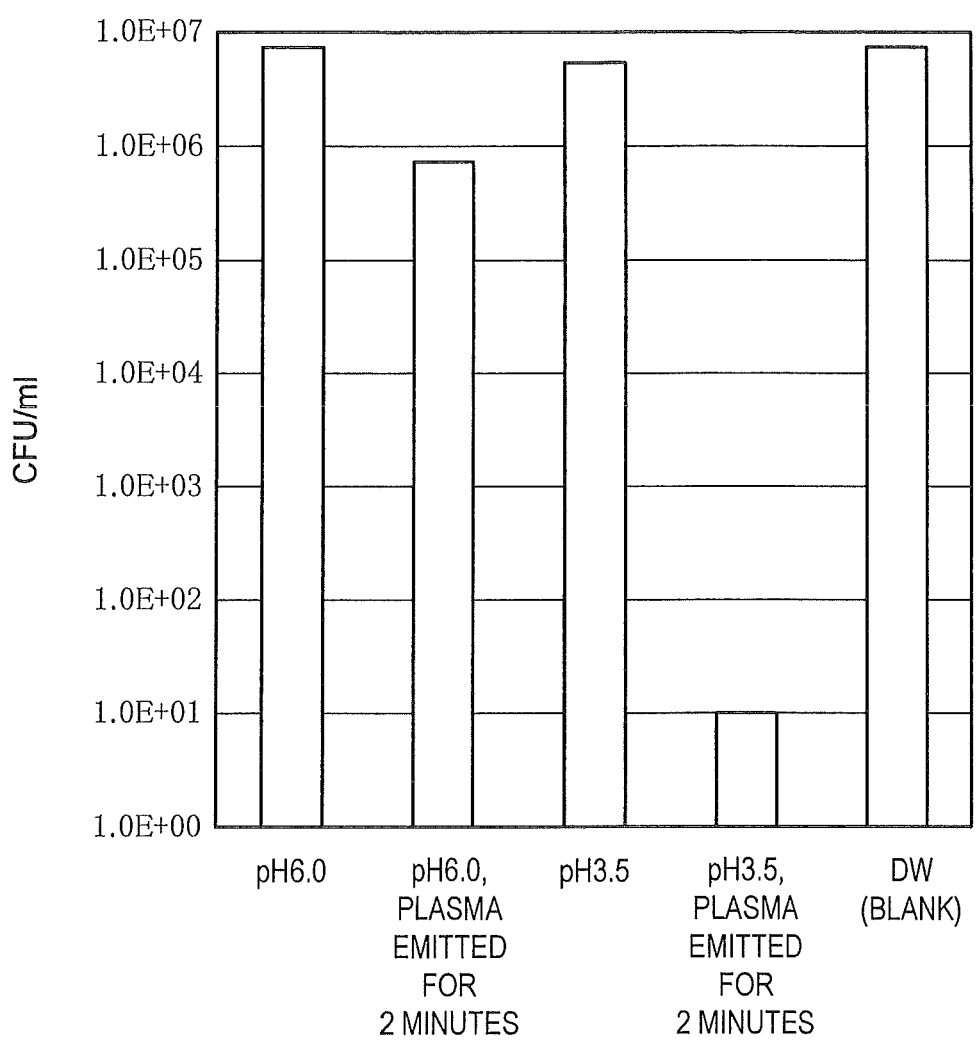
FIG. 7 is a graph of an experimental result illustrating the sterilization effect according to various pH values and the presence or absence of the plasma.

As illustrated in FIG. 7, there is no meaningful difference in the sterilization effect between the respective cases when the sets having pH values at "6.0" and "3.5" are not exposed to the plasma PM. In the case where the pH value is "6.0" and when the set is exposed to the plasma PM, the number of bacteria is decreased to $1/10$ of the original number. However, this does not indicate such a remarkable effect.

In contrast, when the pH value is "3.5" and the set is exposed to the plasma PM, the number of bacteria is decreased to about a millionth. This means a significantly strong microbiocidal activity. To put it differently, the result shows that, when the pH value is adjusted at "3.5" and the set is exposed to the plasma PM, a drastic microbiocidal activity of such an extent that it can be called completely sterilized with respect to the original bacteria concentration of 7,000,000 CFU/ml is attained. This kind of microbiocidal activity in such a short time period is equivalent to relatively strong bactericide and, at the same time, has a very wide applicability because it utilizes the plasma PM whose strength and reaction time can be controlled by parameters externally supplied.

For example, a sterilization target is indirectly sterilized by immersing the target in a liquid whose pH is adjusted or by spraying a liquid whose pH is adjusted onto the target, and thereafter the liquid or the target is exposed to the atmospheric plasma.

EXAMPLE 2

In Example 2, the sterilization effect is examined according to the exposure time during which the liquids having different pH values are exposed to the plasma PM.

(I) Conditions of Experiment (1) Preparation of Bacteria and Evaluation Method of Sterilization

*Escherichia coli* or lactic acid bacteria shaking-cultured using a liquid culture medium for over 18 hours at 30° C. are diluted with sterilized water and adjusted to have a concentration of about $7.0 \times 10^7$ CFU/ml, which is used as microbial suspension.

Usually, turbidity and concentration (CFU/ml) of microorganisms are in a proportional relationship. It is known that, in the case of *Escherichia coli*, when the optical density for light having a wavelength of 600 nm (OD600) is 1.0, the bacteria concentration becomes about $7.0 \times 10^8$ CFU/ml. Therefore, it is possible to obtain microbial suspension having the aforementioned concentration of $7.0 \times 10^7$ CFU/ml by recovering the cultured *Escherichia coil* through centrifugal separation, diluting the suspension by adding thereafter sterilized water so that OD600 becomes 0.1. The relationship between the turbidity (OD600) and concentration (CFU/ml) is about the same for lactic acid.

The microbial suspension is added to 0.45 ml of sterilized water or to 2.0 mM (or 10 mM) or citric acid-NaOH buffer solution whose pH value has been adjusted at a predetermined value, and the mixture is put into a well of a microplate made of polystyrene and having 24 wells. The mixture is exposed to an LF plasma jet (3.0 litters /min, He gas, and a primary voltage of 70V) for a predetermined period of time. The LF plasma jet will be described later.

After being exposed to the plasma, the mixture is recovered, serially diluted, applied onto the agar plate medium, and measured for the number of colonies after sixteen-hour cultivation. To be specific, the recovered microbial suspension is diluted to $1/10$ of concentration by sterilized water, and further diluted to $1/10$ of concentration to thereby produce a diluent having $1/10^2$ of the original concentration. This way, diluents down to $1/10^4$ of the original concentration are prepared, and 0.1 ml each of individual diluents are dispersed on the agar plate medium for overnight cultivation at 30° C.

Eventually, data for 50-500 colonies/plate, which can be considered the most reliable among others, is chosen. Just for reference, when 0.1 ml of the non-diluted mixture, which has the highest concentration, are dispersed, no colonies are detected. In this case, the bacteria concentration is 10 CFU/ml or lower, which is a limit for detection. Since this figure is smaller than 10 CFU/ml, it is considered that this state substantially represents a complete sterilization state. It should be noted, however, that there are some cases in which actual measurements are performed only for the case where the diluent diluted down to $1/10^2$ of the original concentration is dispersed. In such a case, the bacteria concentration of $1.0 \times 10^3$ CFU/ml is regarded as the detection limit.

(2) Exposure to Plasma

The plasma used in Example 2 is called an LF plasma jet. The LF plasma jet was invented by Kitano et al, who are also inventors of the present invention, and is disclosed in International Application PCT/JP2007/061837.

According to the LF plasma jet, it is possible to generate a low-temperature atmospheric plasma jet easily. By exposing a liquid to such plasma to thereby supply various types of active species (electrons, ions, radicals, electric field, etc.) into the liquid, plasma processing in the liquid conventionally unachieved is aimed. Since the LF plasma jet is in a stable state as compared with arc discharges or spark discharges, it is possible to perform plasma processing without physically destroying the liquid itself and substances present in the liquid by heat or shock waves. One example of which is the plasma sterilization according to the present embodiment.

The LF plasma jet uses helium gas. When the LF plasma is jetted into air, oxygen and nitrogen are respectively energized and thereby excited to possibly become reactive species. For example, only jetting the plasma in the air causes ozone to be generated and accompanying smell of ozone as well. In order to evaluate what is described above, evaluation is performed on the influence of the atmospheric gas by not only emitting the plasma in a jet form but also arranging an atmospheric gas with the helium gas alone or the helium gas mixed with air. In the drawings, the results of sterilization experiments illustrated in the same drawing indicate that the experiment is conducted under the same plasma generation condition. However, the results of experiments illustrated in different drawings do not necessarily mean that the same plasma generation condition is used.

Example 2 is implemented by using the LF plasma jet having a variety of characteristics as described above. When the reaction mechanism is verified scientifically, it is finally found that any type can be used as long as it is plasma.

Detailed description of the LF plasma jet will be given later.

(3) Other Types of Plasma Can be Used

An evaluation of biocidal activity can be performed through a similar operation even when mixture is prepared according to the conditions described above and the liquid is processed using a plasma source other than the LF plasma jet (e.g., a chamber-type plasma emitting device).

However, when the influence of the pH described later is taken into account, such a powerful microbiocidal effect can not be expected from the exposure to plasma in a non oxygen-containing atmosphere. Accordingly, a system for supplying oxygen in some form or another is necessary. In an experiment using the chamber-type plasma emitting device and when plasma with only a helium gas is emitted, the microbiocidal activity is relatively low even in the case where the pH is adjusted. On the contrary, when air is mixed therewith, extremely high biocidal activities are obtained. From this result, it is found that nitrogen included in the air also plays a role in providing the biocidal activities.

However, how the oxygen is supplied is not restricted to a method in which the oxygen gas is simply mixed with the plasma gas. It is also considered effective, for example, to increase in advance dissolved oxygen in a liquid by means of microbubbles, add a reagent which is supposed to supply oxygen into the liquid by chemical reaction, or the like. By using such a method, an increase in microbiocidal activity by way of adjusting the pH value is expected even when a plasma source that discharges directly in the liquid is used.

(II) Change in Sterilization Performance According to a Change in pH

According to a result of evaluating the microbiocidal activity on *Escherichia coli* at various pH values (7.8 to 3.5), it is observed that the lower the pH value is, the stronger the microbiocidal activity tends to become, and the effect of which is found to be noticeable at a pH value of about 4.5. This value is slightly toward the acidity side from the pKa of 4.8 in the equilibrium reaction between the superoxide anion radicals ($O_2^-$.) and the hydroperoxy radicals (HOO.) shown in Formula 1 presented above.

Figure 8:
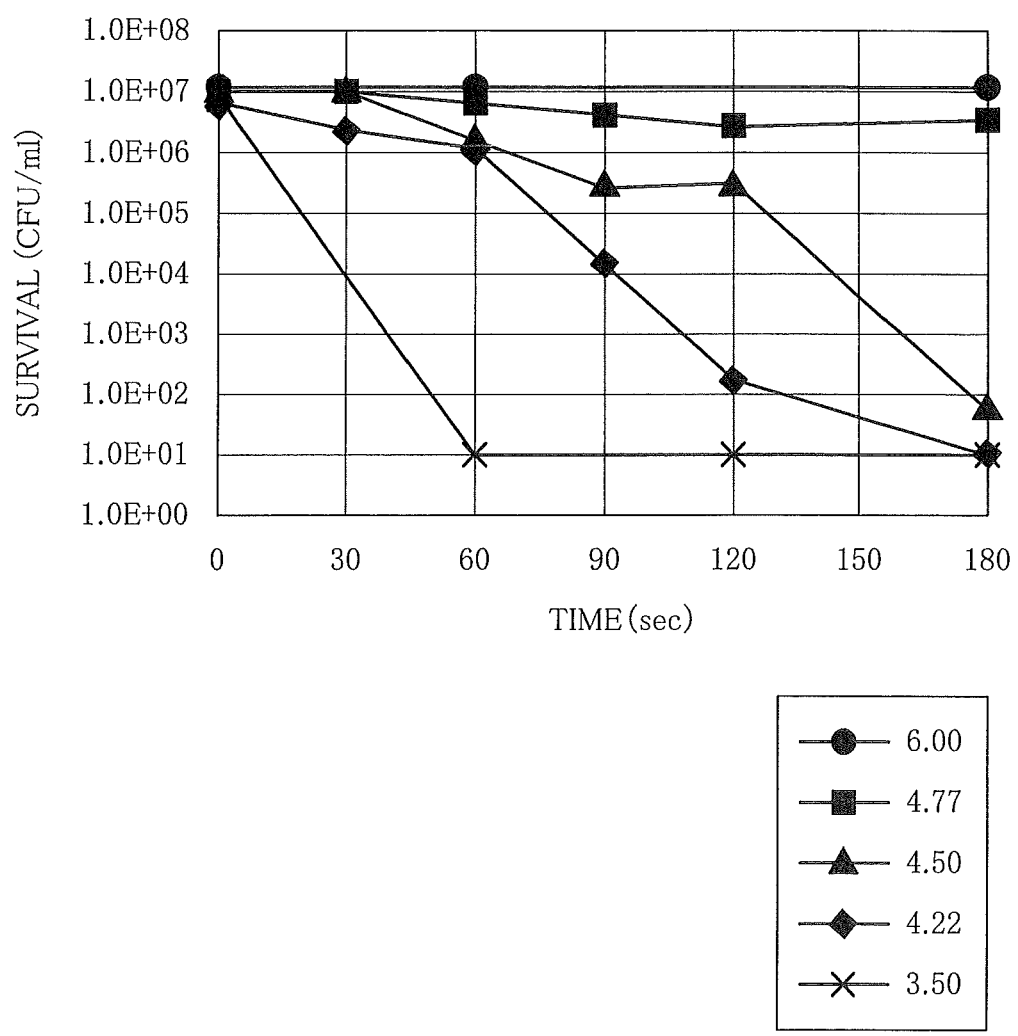
FIG. 8 is a graph comparing microbiocidal activities by plasma on *Escherichia coli*.
Figure 9:
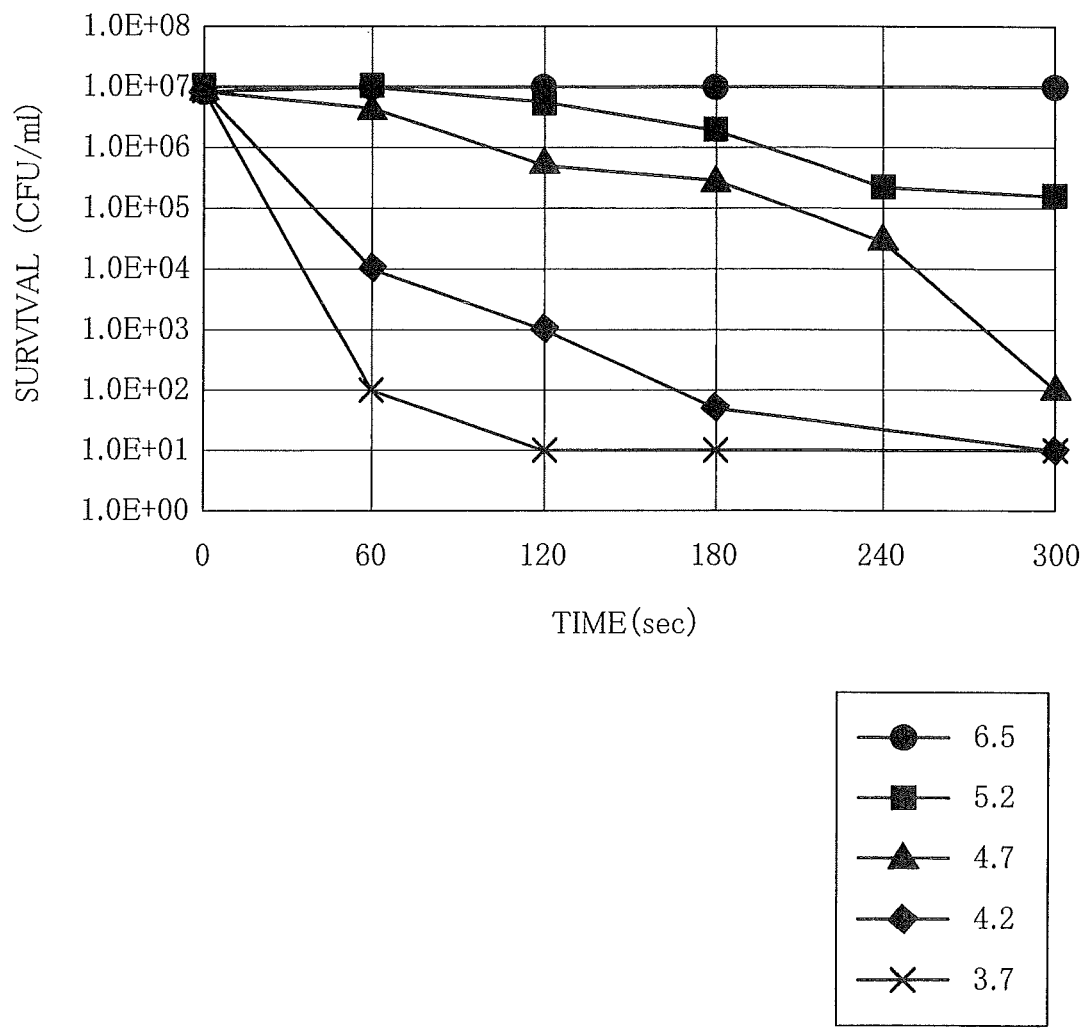
FIG. 9 is a graph comparing microbiocidal activities by plasma on *Escherichia coli*.
Figure 10:
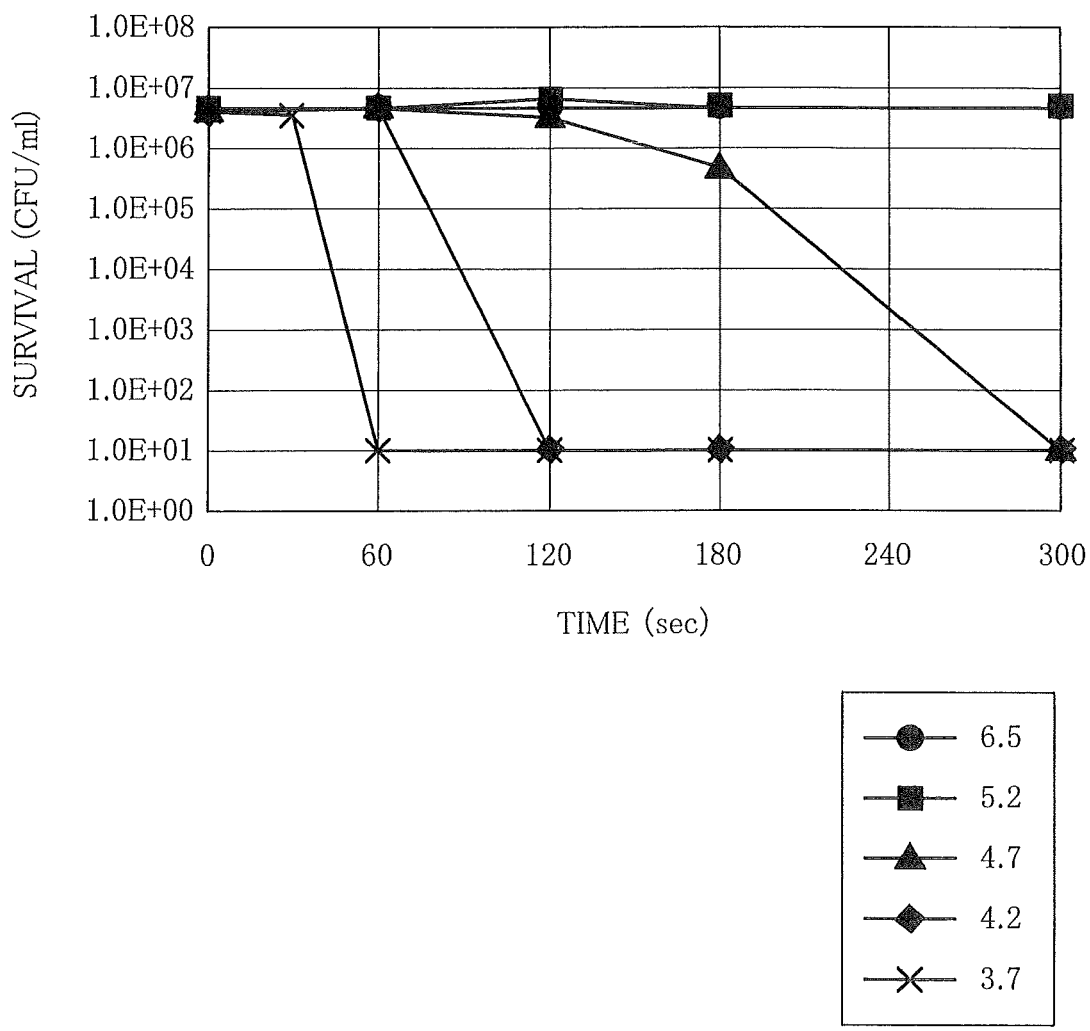
FIG. 10 is a graph comparing microbiocidal activities by plasma on lactic acid bacteria.
Figure 11:
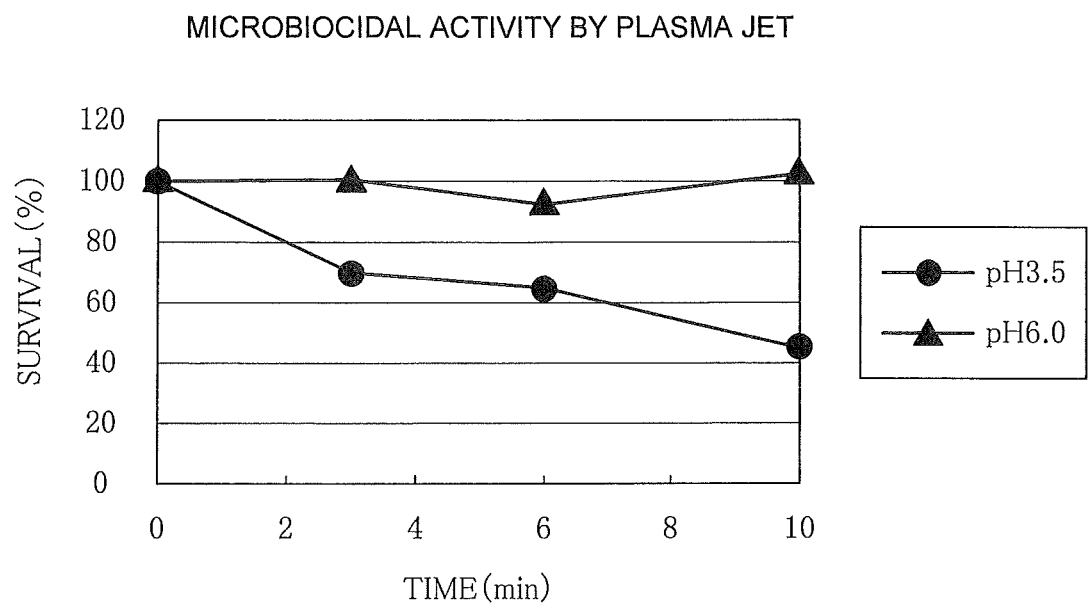
FIG. 11 is a graph comparing microbiocidal activities by plasma on spores of *Bacillus subtilis*.

FIGS. 8-11 illustrate experimental results comparing the microbiocidal activities by the LF plasma jet when the pH of the liquids are maintained at different constant values. FIGS. 8 and 9 are graphs comparing microbiocidal activities on *Escherichia coli*, FIG. 10 is a graph comparing microbiocidal activities on lactic acid bacteria, and FIG. 11 is a graph comparing microbiocidal activities on spores of *Bacillus subtilis*. In FIGS. 8-11, the horizontal axis shows plasma exposure time in seconds.

As illustrated in FIG. 8, when the pH value of the buffer solution is 4.77 or higher, little change in the microbiocidal activity is observed under different pH values, and the D value is 650 seconds when the pH value is 4.77. On the other hand, when the pH value is 4.5 or lower, the microbiocidal activity is drastically enhanced and further enhanced depending on the changes in pH. The D values at pH values of 4.50, 4.22, and 3.5 are 27, 15, and 7 seconds, respectively. It is found that the microbiocidal activity increases by, as large as 24 times when the pH value changes from 4.77 to 4.50. The sterility assurance time is decreased from 130 minutes to 5.4 minutes. Furthermore, about 4-fold improvement is also observed when the pH value changes from 4.5 to 3.5.

According to FIG. 9, little change is observed in microbiocidal activity depending on pH values when the pH of the buffer solution is 5.20 or higher, and the D value is 150 seconds at a pH value of 5.2. On the other hand, when the pH value is 4.7 or lower, the microbiocidal activity is increased and further increased depending on the change in pH value. The D values at pH values of 4.7, 4.2, and 3.7 are 58, 35, and 13 seconds, respectively. It is found that the microbiocidal activity increases by about 10 times when the pH value changes from 5.2 to 3.7. The sterility assurance time is decreased from 23 minutes to 2.6 minutes.

The above-mentioned results indicate that the microbiocidal activity by the plasma does not depend on the pH values at least under the condition in which the pH value is 7.8-4.77. However, the change in pH sharply contributes to the enhancement of the microbiocidal activity when the pH value is 4.5 or less. This means that the sterilization effect by the plasma can be significantly increased by adjusting the pH value of a liquid to be sterilized to become 4.5 or lower.

Further, as shown in FIG. 10, a similar experiment is conducted on lactic acid bacteria, and no sterilization effect by the plasma exposure is observed when the pH of the buffer solution is 5.2 or higher. On the other hand, the microbiocidal activity is attained when the pH value is 4.7 or lower, and the sterilization effect is significantly increased depending on the change in pH value The D values at pH values of 4.7, 4.2, and 3.7 are 31, 10, and 5 seconds, respectively. It is found that the microbiocidal activity increases by about 6 times when the pH value changes from 4.7 to 3.7.

In FIG. 11, when a similar experiment is conducted on spores of *Bacillus subtilis*, no increase in sterilizing activity caused by plasma exposure is observed at a pH value of 6.0. However, it is found that an increase in microbiocidal activity is achieved at a pH value of 3.5 with plasma exposure.

As described above, enhancement in microbiocidal activity is confirmed not only on *Escherichia coli* but also on lactic acid bacteria and spores of *Bacillus subtilis* by adjusting the pH value.

(III) Sterilization by Radicals (1) Hydroperoxy Radicals Formed from Superoxide

Although various factors are pointed out about sterilization in liquid by plasma, active species such as radicals or the like that are secondarily-generated from the plasma are deemed to have a large part of the microbiocidal activity because the plasma (ions and electrons), per se, can not penetrate into the liquid.

Hydroxyl radicals (OH.) are radicals that are highly reactive but can barely move in a solution because the hydroxyl radicals have a shorter life time. For this reason, it is considered that the hydroxyl radicals (OH.) are produced only in the vicinity of a surface of the liquid where the plasma makes contact with the liquid. It is found, from a result of the experiment, that the biocidal activity penetrates in a depth direction by 1.0 cm or more. Accordingly, another type of active species having a longer life time is supposed to be involved.

Contrary to the hydroxyl radicals (OH.), superoxide anion radicals ($O_2^-$.) have a relatively longer life time and it is considered that they can exist even in water for a few seconds. Although the superoxide anion radicals ($O_2^-$.) can be produced easily when oxygen in the air is excited by the plasma, the superoxide anion radicals, per se, have low reactivity and a fairly low microbiocidal activity. However, the superoxide anion radicals ($O_2^-$.) are considered to react with hydrogen ions ($H^+$) in the water and maintain the equilibrium state shown by Formula (1) discussed above.

To be specific, the superoxide anion radicals ($O_2^-$.) react with the hydrogen ions ($H^+$) in the liquid to form hydroperoxy radicals (HOO.). The hydroperoxy radicals (HOO.) are known to have an extremely strong microbiocidal activity. According to one theory, the hydroperoxy radicals (HOO.) are said to have microbiocidal activity 100,000 times strong as that of the superoxide anion radicals ($O_2^-$.). Moreover, the equilibrium state shown in Formula (1) indicates that the higher the concentration of the hydrogen ions ($H^+$) becomes, i.e., the lower the pH value becomes, the greater the amount of the hydroperoxy radicals (HOO.) increases.

Since the value representing the equilibrium constant of the equilibrium reaction shown in Formula (1) above, i.e., pKa, is 4.8, such an effect is expected to dramatically increase at a pH value equal to or lower than 4.8, which truly coincides with a result of the experiment where the microbiocidal activity sharply increases at a pH value of 4.5 or lower. To put it differently, as long as the pH is 4.8 or higher, a majority part of the superoxide anion radicals ($O_2^-$.) is dissociated from hydrogen, and a majority part of the superoxide anion radicals ($O_2^-$.) is combined with the hydrogen, which forms the hydroperoxy radicals (HOO.) when the pH becomes 4.8 or lower.

The improvement of the microbiocidal activity by the plasma depending on the decrease in pH is considered to be attributable to such a mechanism. To verify this, a sterilization experiment is conducted by adding superoxide dismutase (SOD), an enzyme having a function of causing a reaction between the superoxide anion radicals ($O_2^-$.) and water and converting them into hydrogen peroxide. In other words, by conducting an experiment using the SOD, it is possible to evaluate the microbiocidal activity of the superoxide anion radicals ($O_2^-$.). The result of the experiment is illustrated in FIG. 12.

Figure 12:
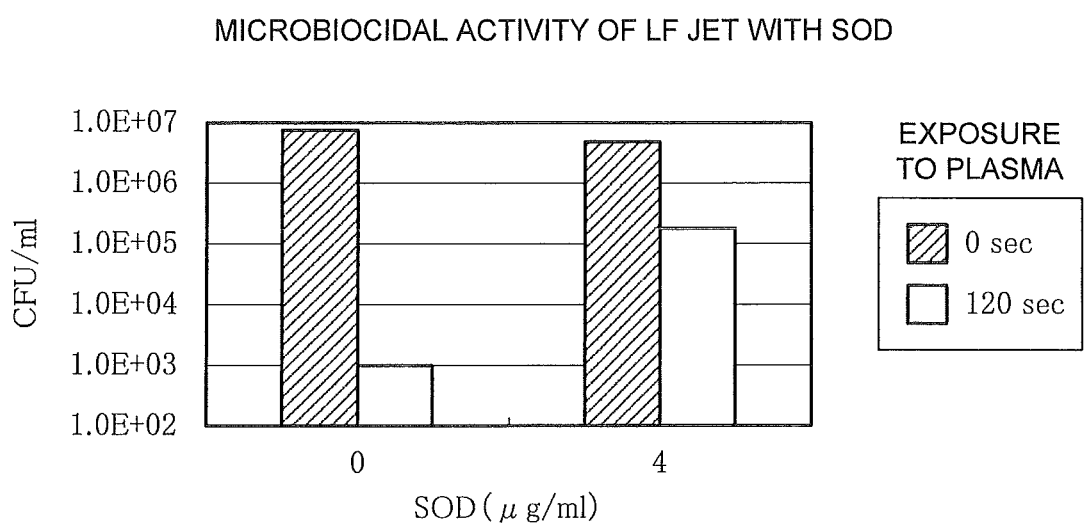
FIG. 12 is a graph of an experimental result obtained by comparing microbiocidal activities when superoxide dismutase (SOD) is added.

In FIG. 12, in the case where the SOD is not added but the plasma is emitted for 120 seconds, the number of bacteria is decreased to 1/10,000. However, in the case where 4 µg/ml of SOD is added and the plasma is exposed for 120 seconds, the number of bacteria is merely decreased to 1/100 or less. From this, it is found that there is an improvement in survival rate of bacteria by at least 100 times by adding the SOD.

It should be noted, however, that, since the limit for detection is $1.0 \times 10^3$ CFU/ml, the number of bacteria is actually reduced more when the SOD is not added but the plasma is emitted. For this reason, the improvement in survival rate of bacteria is expected to be 10,000 times or more when the SOD is added.

This indicates that the superoxide anion radicals ($O_2^-$.) exert a great influence on biocidal activity, and suggests the involvement of the hydroperoxy radicals (HOO.).

From the foregoing discussion, it is considered that, in the sterilization in liquid by plasma, the superoxide anion radicals ($O_2^-$.), one type of oxygen radical, are combined with the hydrogen ions ($H^+$) in the liquid to form the hydroperoxy radicals (HOO.) to thereby show the microbiocidal effect. The effect is considered to be dramatically enhanced by raising the concentration of the hydrogen ions ($H^+$), i.e., lowering the pH. It is important that such a pH should be lower than 4.8 which is a value of pKa in the equilibrium reaction represented by Formula (1) described above. From the results of the experiment illustrated in FIGS. 8-11, it is preferable that the pH be 4.8 or lower, and it is more preferable that the pH be 4.5 or lower.

(IV) Evaluation of NOx and $H_2O_2$

When the LF plasma jet is emitted in the air, the nitrogen in the air is oxidized by the plasma to become $NO_2$. The $NO_2$, by dissolving in water, turns to $HNO_2$ or $HNO_3$, which reduces the pH value as a result. In addition, since dissolved nitrogen included in the water is also oxidized under the influence of the plasma, a slight reduction in pH is caused even with the plasma exposure in an atmosphere that does not contain nitrogen. However, the reduction in pH from this kind of cause is not constant due to a change in the environment in which the plasma is used or a change in volume of an object to be sterilized. Therefore, it is difficult to define the sterilization time. Further, when compared with the case in which the pH is adjusted at 3.5 in advance, it is confirmed by the experiment that it takes longer time for achieving sterilization. Above all, the reduction in pH caused by $NOx^-$ does not influence the effect of enhancement in microbiocidal activity of a buffer solution having a pH value adjusted at 4.8 or lower in advance.

Other than what is described above, it is found that $H_2O_2$ is also generated as a result of a reaction between oxygen and water with plasma exposure. However, the amount of $H_2O_2$ thus generated under the condition of the sterilization experiment is merely 50 mg/l at the maximum, which is not such a concentration that affects the sterilization effect. In addition, the amount of produced $H_2O_2$ is constant regardless of the pH value.

(V) Conclusion (1) Synergistic Effect Between pH Adjustment and Sterilization by Plasma Sterilization by plasma can be divided into two cases, i.e., (a) the plasma directly exerts influences on microorganisms, and (b) active species such as radicals that are generated secondarily exert influences.

In the case of (a), the plasma barely works in the liquid and on a target that has a complicated structure. On the other hand, the active species generated secondarily can act upon the microorganisms in the liquid by dissolving therein. The superoxide anion radicals ($O_2^-$.) having a relatively longer life time in the aqueous solution are combined with the hydrogen ions ($H^+$) to turn into the hydroperoxy radicals (HOO.) having an extremely powerful microbiocidal activity, and the concentration of which depends on the concentration of the hydrogen ions ($H^+$), that is, pH.

Particularly, since pKa of the equilibrium reaction expressed in Formula (1) above is 4.8, a proportion of the hydroperoxy radicals (HOO.) is expected to increase in a case where pH is lower than that value. For example, in the case where the pH is 4.8, the abundance ratio of the hydroperoxy radicals (HOO.) to the superoxide anion radicals ($O_2^-$.) is 1 to 1. However, the ratio becomes 2 to 1 at a pH value of 4.5 and 20 to 1 at a pH value of 3.5. In this way, the abundance ratio of the hydroperoxy radicals (HOO.) having a strong microbiocidal activity increases depending on the pH value.

Accordingly, it is possible to significantly increase the microbiocidal activity by plasma by adjusting pH of a liquid at 4.8 or lower (ideally at 3.5 or lower) when the liquid or a target in the liquid is sterilized by bringing the plasma into contact with the liquid. Further, the chemical agents used for adjusting the pH are not particularly limited, and such chemical agents are not required at all to have a microbiocidal activity or oxidizability.

[Second Embodiment]

In the Second Embodiment described hereinafter, a description will be given of an example in which the sterilization method is applied to a living body.

Here, microorganisms present on a surface of a living body or in the vicinity thereof are sterilized. Such a sterilization method is implemented by a step of applying a liquid having a pH value of 4.8 or lower to the surface of the living body and a step of exposing a liquid present on the surface of the living body to low-temperature plasma. Hereinafter, a description will be given of a method for sterilizing wounds of a human body by using a gel-patch.

More often than not, a wound with seriously damaged skin by burn or bedsore is accompanied by infection. It is possible to sterilize such a wound, without using a bactericide or an antibiotic, by exposing the wound to the LF plasma jet. In doing so, by applying an acidic liquid to the human body beforehand, effective sterilization is expected, and a sterilization effect not only on the surface of the skin but also inside is expected. The following method is used to prevent the human body from the influence exerted by the plasma.

Figure 13:
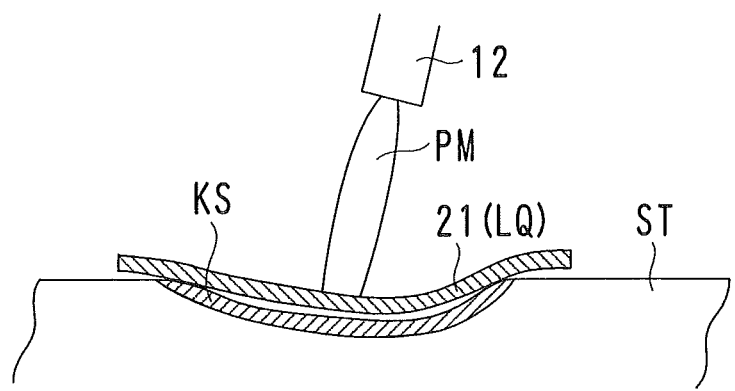
FIG. 13 is a diagram depicting a sterilization method according to the second embodiment of the present invention.

As illustrated in FIG. 13, a gel-like gelatin sheet 21 that is swelled by an acidic liquid (pH of about 3.5) is put on a wound KS of a living body ST, and the plasma PM is emitted thereto.

The gelatin sheet 21 is produced by, for example, dissolving gelatin in an acidic aqueous solution having a pH value of about 2-4.5 and molding the resultant into a sheet having a thickness of about one to a few millimeters. With this gelatin sheet 21, a liquid having a adjusted pH value is applied to the surface of the living body ST. It is also possible to use such a gelatin sheet available on the market for medical use.

When the gelatin sheet 21 is exposed to the plasma PM, superoxide anion radicals ($O_2^-$.) are supplied and accompanied by the reaction expressed in Formula (1) in the gelatin sheet 21. As a result, hydroperoxy radicals (HOO.) are produced with which the microorganisms in the wound KS are sterilized efficiently. The plasma exposure may be performed, for example, for a period of about one to a few minutes, which enables the sterilization of the wound within a short period of time.

Alternatively, as a method for applying an acidic liquid to the wound KS, an acidic aqueous solution having a pH value of about 2 to 4.5 may be applied to the wound KS by a brush in lieu of or together with the gelatin sheet 21.

Although the acidic aqueous solution may be applied in advance, an acidic material may be gradually applied in a form of a liquid or a gas though a tip of a pen or the like during the operation.

Alternatively, a rolled sheet moistened with an acidic liquid is applied to the wound KS, and the wound KS is exposed to the plasma indirectly through the rolled sheet. Here, the rolled sheet is arranged to be sequentially fed so that a fresh sheet is used at any time.

[Third Embodiment]

In the third embodiment, a description will be given of a method for performing sterilization after turning a tooth, dental pulp, or gum acidic.

The sterilization method adopting adjustment of pH and the plasma PM is applicable not only to simple sterilization of the skin surface but also a dental treatment. It is recognized that what is required is complete sterilization but not normal microbiocidal treatment of a tooth, dental pulp, or gum. Conventionally, sterilization is performed using chemical agents, which causes a postoperative infectious disease due to insufficient sterilization. In contrast, a new completely sterilizing effect is expected from the sterilization using the pH adjustment and the plasma PM.

Specifically, the pH value of the tooth, dental pulp, or gum is adjusted to become acidic, and the plasma is emitted thereto. For example, an acidic aqueous solution having a pH value of about 2-4.5 is coated or injected to or around the tooth, dental pulp, or gum, or the acidic aqueous solution is used for gargling to turn these areas acidic.

When the tooth, dental pulp, or gum is exposed to the plasma PM, hydroperoxy radicals (HOO.) are produced on or around the tooth, dental pulp, or gum, which performs complete sterilization.

If necessary, sterilized water is used for rinsing, and thereafter the tooth, the dental pulp, or the like is sealed to complete the treatment.

Next, a sterilization apparatus 1B used for dental treatment will be described.

When the plasma generation device 12 is used to perform sterilization, there is a possibility that a toxic gas such as ozone or $NO_x$ is generated as a byproduct along with generation of the plasma PM. This means that, when the sterilization method according to the present embodiment is applied near someone's presence, it is necessary to provide a device for exhausting such gases. Particularly, when the method is applied to the dental treatment or the like, plasma processing is performed in the oral cavity of a patient. Therefore, it is necessary to enclose a portion subjected to the plasma processing so that the toxic gas does not leak into the oral cavity.

Figure 14:
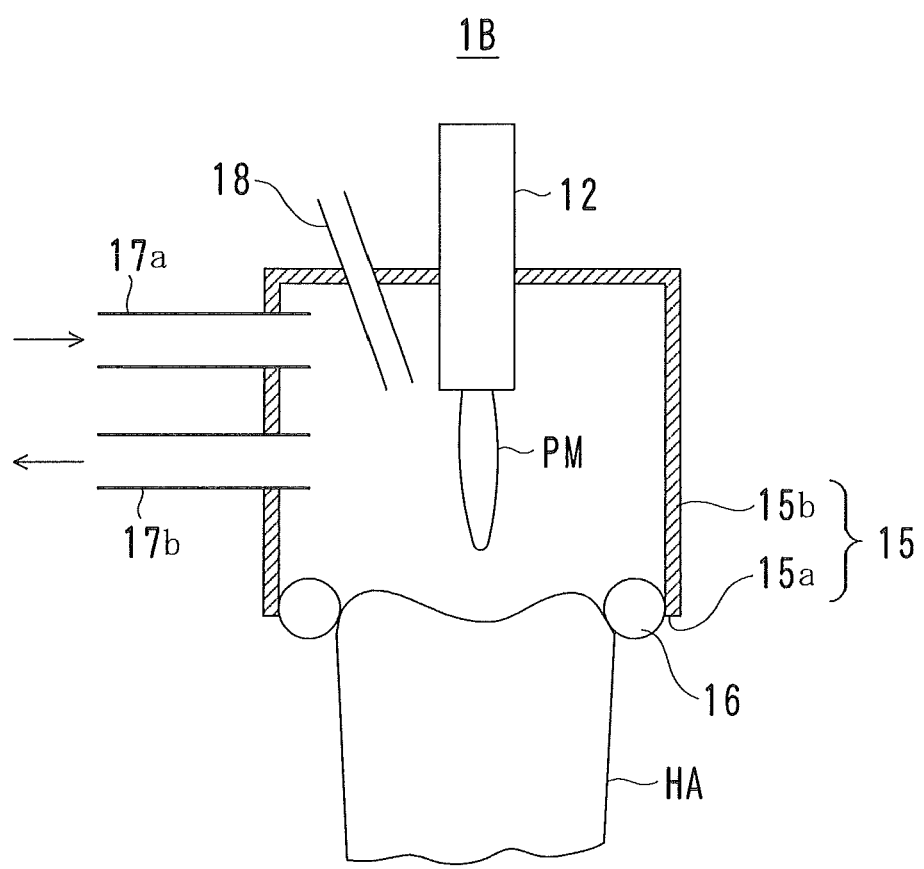
FIG. 14 is a diagram illustrating another configuration example of the sterilization apparatus.

With reference to FIG. 14, the sterilization apparatus 1B includes a plasma generation device 12, a housing 15, a seal member 16, an atmospheric gas introduction pipe line 17a, a gas exhausting pipe line 17b, and a pH adjustment pipe line 18.

The plasma generation device 12 generates the plasma PM within the housing 15. The timing at which the plasma PM is generated is controlled by means of an unillustrated control mechanism automatically or based on the instructions of the operator.

The housing 15 has a container-like shape having, at one portion thereof, an opening 15a so that a surface of a part of a tooth HA to be targeted is surrounded and hermetically enclosed. Although the opening 15a should be shaped in accordance with a shape of the tooth HA, a periphery of a body portion 15b may be arranged in a cylindrical shape, a rectangular envelope shape, a spherical shape, or the like. The housing 15 may be formed by molding using such a material as a synthetic resin or glass.

The seal member 16 is provided in the opening 15a of the housing 15 and seals a gap between the opening 15a and the tooth HA to maintain airtightness of the housing 15. The seal member 16 may be produced using silicon rubber, other synthetic rubber, synthetic resin, or the like. An O-ring, another type of sealing member, or a gasket may be used as the seal member 16. It is also possible to form the housing 15 integrally with the seal member 16.

The atmospheric gas introduction pipe line 17a is a pipe line for introducing an atmospheric gas containing nitrogen gas into the housing 15. An amount of the atmospheric gas, timing at which the gas is introduced, or the like through the atmospheric gas introduction pipe line 17a is controlled by means of an unillustrated atmospheric gas control mechanism automatically or based on the instructions of the operator.

The gas exhausting pipe line 17*b* is a pipe line for exhausting the atmospheric gas inside the housing 15 to outside. It is possible to use a flexible tube made of a synthetic resin or a synthetic rubber for the atmospheric gas introduction pipe line 17*a* and the gas exhausting pipe line 17*b*.

The pH adjustment pipe line 18 is a pipe line for feeding a pH adjustment substance so that at least a part of the tooth HA as a target is adjusted to have a pH value of 4.8 or lower. The opening at a tip end of the pH adjustment pipe line 18 is directed toward the surface of the tooth HA to be treated. A liquid containing acid or salt, a gas such as carbonic acid gas, and other chemical agents can be used as the substance that is fed through the pH adjustment pipe line 18. If the substance used for adjusting the pH is a gas, it is preferable that the surface of the tooth HA be moistened in advance. An amount of the substance to be fed through, timing at which the gas is introduced, or the like is controlled by means of an unillustrated substance control mechanism automatically or based on the instructions of the operator.

A description will be given of how to operate the sterilization apparatus 1B and how the apparatus 1B operates.

First, while the patient keeps his/her mouth opened, the operator places the housing 15 of the sterilization apparatus 1B over the tooth HA which is a target for treatment. Then, the substance is supplied through the pH adjustment pipe line 18 and decreases the pH value of the surface of the tooth HA to 4.8 or lower. An atmospheric gas containing nitrogen gas, for example, the air, is fed into the housing 15. Along with this, the plasma PM is generated by the plasma generation device 12. The atmospheric gas, and toxic gases etc. produced by plasma processing are exhausted to outside through the gas exhausting pipe line 17*b* so as not to leak into the oral cavity.

Radicals produced by the plasma PM make contact with the surface of the tooth HA, and the hydroperoxy radicals (HOO.) and the peroxynitrite (ONOOH(ONOO⁻)) as described above are generated, which sterilize the tooth HA.

Since the plasma processing by the plasma generation device 12 is carried out in a space hermetically enclosed by the housing 15 and the seal member 16, a toxic gas, even if generated, is exhausted to outside through the gas exhausting pipe line 17*b* and does not leak into the oral cavity. Consequently, there is no chance of the patient to inhale the toxic gas, and, as a result, unnecessary damage caused to the respiratory system can be avoided.

In this way, by using the sterilization apparatus 1B having an airtight structure, it becomes possible to perform sterilization only on a specific part.

In the sterilization apparatus 1B described above, the pH adjustment pipe line 18 is provided, through which a substance for decreasing the pH is also supplied. However, it is also possible to provide a pipe line that can be opened and closed or merely a hole as the pH adjustment pipe line 18. Then, the operator inserts a nozzle of an injector or an atomizer into the pipe line or the hole and manually operates the injector or the atomizer to thereby feed the substance.

Alternatively, instead of providing such a dedicated pH adjustment pipe line 18 in the housing 15, a gas supply pipe 31 may be used for feeding the substance as well.

Figure 15:
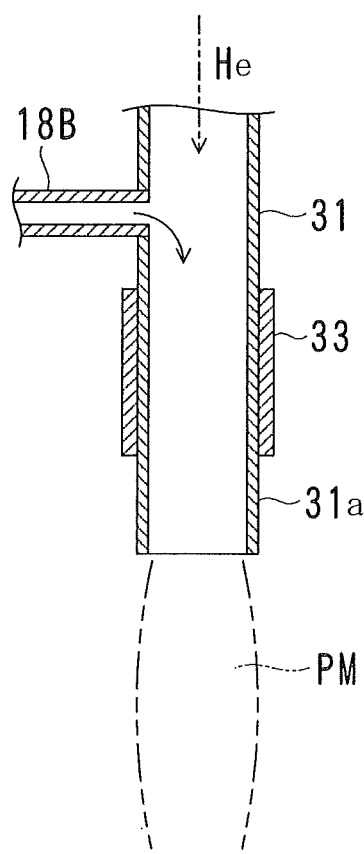
FIG. 15 is a diagram illustrating another example of the plasma generation device used in the configuration illustrated in FIG. 14.

For example, in a plasma generation device 12B illustrated in FIG. 15, a pH adjustment pipe line 18B is provided in a manner to branch off from the gas supply pipe 31 in an upper portion of a high-potential electrode 33. Although the gas supply pipe 31 is used for supplying helium gas when the plasma PM is generated, a substance for adjusting the pH value is supplied from the pH adjustment pipe line 18*b* to the tooth HA via the gas supply pipe 31 prior to generating the plasma PM. For this purpose, an on-off valve or a passage changeover valve is provided in a portion upstream of the pH adjustment pipe line 18B and the gas supply pipe 31.

It is to be noted that how the pH adjustment pipe line 18B branches off from the gas supply pipe 31, a position and an angle of the branch, sizes of individual pipes, and so on may be decided in a diversifying manner differently from what are illustrated in FIG. 15. The gas supply pipe 31 and the high-potential electrode 33 will be described later with reference to FIG. 19.

When such a plasma generation device 12B is used, the sterilization apparatus 1B is placed over the tooth HA, thereafter a substance for adjusting the pH value is supplied through the pH adjustment pipe line 18B, and then helium gas is supplied to the gas supply pipe 31 to generate the plasma PM.

It is also possible for the operator to supply the substance for adjusting the pH value without providing such pH adjustment pipe lines 18 or 18B. For example, a liquid having a pH value of 4.5 or lower is infiltrated in absorbent cotton and applied to the tooth HA. Alternatively, a liquid or a gas for adjusting the pH is sprayed onto the tooth HA using an atomizer or the like. Thereafter, the sterilization apparatus 1B is placed over the tooth HA, and plasma processing is performed.

Hereinbefore, the description has been given of a case in which the target of the sterilization apparatus 1B is the tooth HA. It is also possible to arrange a biological part other than the tooth HA or a non-biological object as the target.

[Fourth Embodiment]

In the fourth embodiment, a description will be given of a method for performing sterilization by applying an acidic liquid to medical devices.

Figure 16:
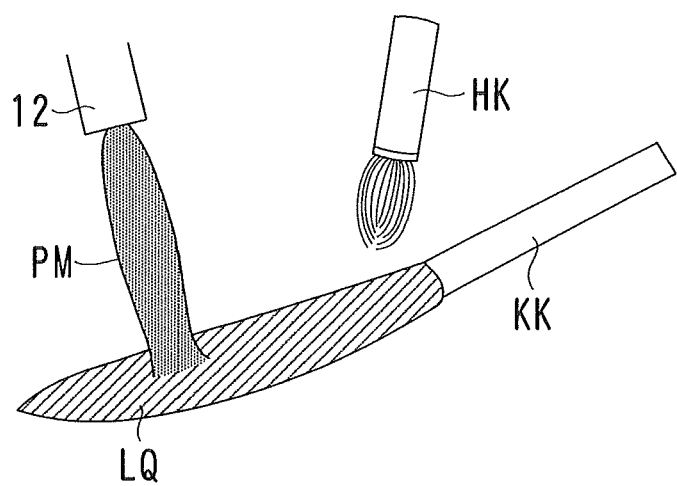
FIG. 16 is a diagram depicting a sterilization method according to the fourth embodiment of the present invention.

As illustrated in FIG. 16, an acidic liquid having a pH value of about 1-4.5 is coated on a surface of a device KK with a brush HK, and the device KK is exposed to the plasma PM from the plasma generation device 12.

With this arrangement, hydroperoxy radicals (HOO.) are produced on a surface of the device KK to thereby sterilize the device KK.

It is also possible to mix polymers into an acidic liquid to increase the viscosity thereof and pectize it so as to prevent the acidic liquid from diffusing from the device KK. The resultant can also be applied. Alternatively, in order to generate an acidity state on the surface of the device KK, the acidic liquid may be sprayed thereto using an atomizer, or the device KK may be immersed in the acidic liquid for a predetermined period of time.

[Fifth Embodiment]

In the fifth embodiment, a description will be given of a method for performing sterilization while a medical device is immersed in an acidic liquid.

Figure 17:
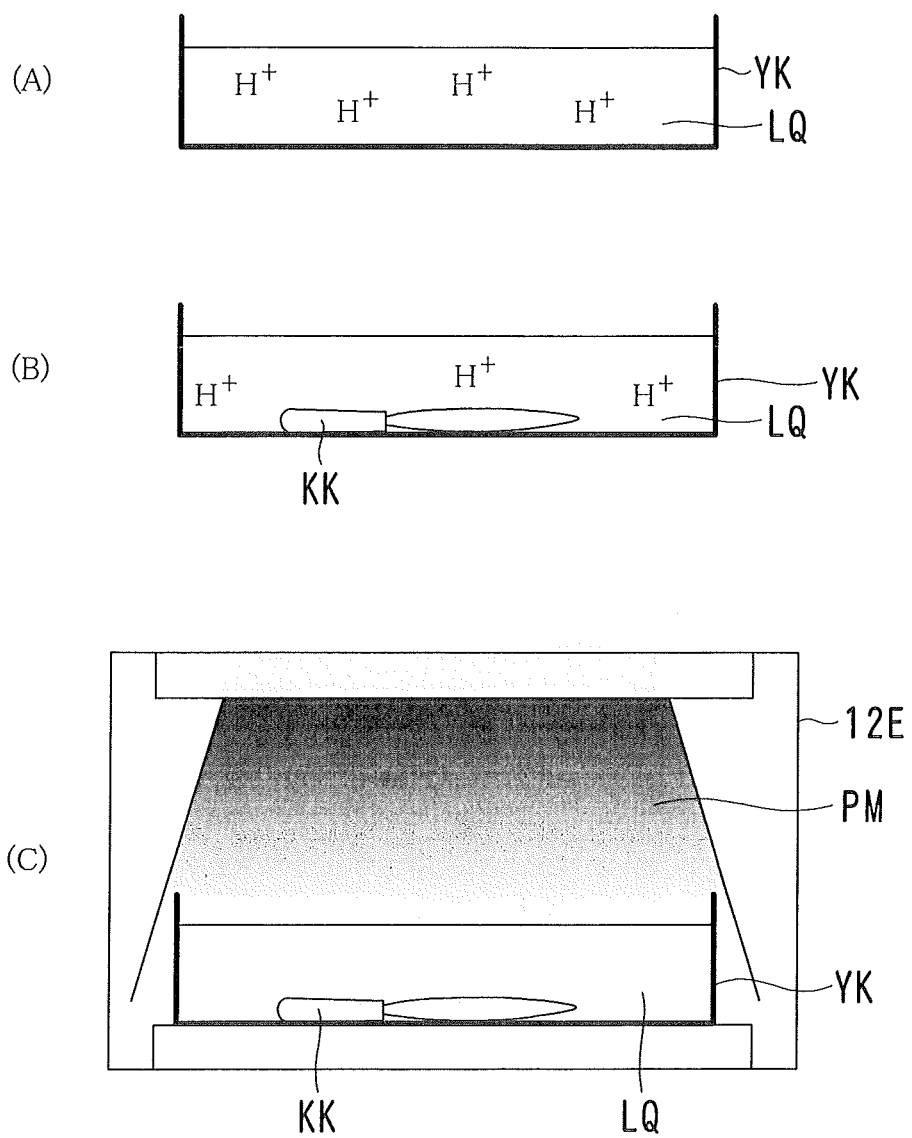
FIG. 17 is a diagram depicting a sterilization method according to the fifth embodiment of the present invention.

As illustrated in FIG. 17(A), a container YK is provided with an acidic liquid LQ having a pH value of about 1-4.5. As illustrated in FIG. 17(B), a device to be sterilized is put into the container YK and immersed in the liquid LQ. As illustrated in FIG. 17(C), the entirety of the container YK is carried into a plasma generation device 12E, and the plasma PM is made contact with a surface of the liquid LQ.

With this arrangement, hydroperoxy radicals (HOO.) are produced in the liquid LQ, and sterilization of the device KK is performed.

The plasma generation device 12E is filled with helium gas and a mixed gas containing small amounts of nitrogen and oxygen. Therefore, the plasma PM with helium gas serving as a medium gas is generated. However, other gasses than the helium gas may be used. It is preferable that the depth of the container YK be shallow so that the hydroperoxy radicals (HOO.) produced in the liquid LQ by the action of plasma PM can sufficiently reach the surface of the device KK. However, even with a substantial depth, sufficient agitation compensates it.

Hereinbefore, the first to fifth embodiments have been described. Hereinafter, various variation examples of the elements or examples of applications that can be applied to these embodiments or other types of embodiments will be described.

[Sterilization Utilizing Neutral Helium Metastable to Prevent Electric Current from Being Caused by Charged Particles]

Instead of directly exposing an acidic liquid to plasma, the liquid is exposed to metastable atoms that are in a metastable state of a noble gas such as helium to thereby promote generation of radicals in the liquid. When the LF plasma jet is used, charged plasma particles themselves are prevented from being emitted by using an electrode arrangement adopted for a so-called reverse jet so that unnecessary damage caused to human cells is reduced. The reverse jet is produced by arranging a ground electrode in the vicinity of a plasma jetting port so that an electric field does not leak outside. By this arrangement, unnecessary emission of charged particles can be controlled.

Oxygen-based radicals exerting sterilization ability are generated when the metastable collides with oxygen molecules or water molecules in the air.

Further, by mixing a small amount of oxygen gas or nitrogen gas into a plasma-generating gas in the reverse jet, various types of radicals are generated in a plasma discharging portion. The liquid is exposed to only these radicals to make it a safer type of discharge.

[Shape of a Chamber of a Plasma Generation Device]

Figure 18:
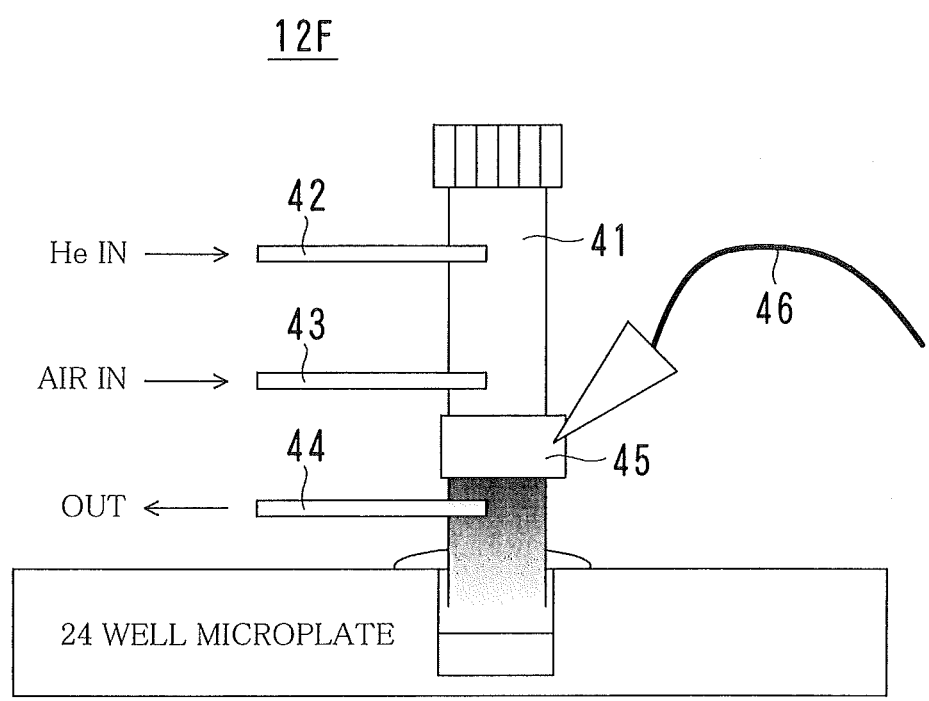
FIG. 18 is a diagram illustrating an example of a chamber of the plasma generation device.

A chamber of a plasma generation device 12F has a shape as illustrated in FIG. 18.

Referring to FIG. 18, helium is supplied into a chamber 41 through a helium pipe line 42 located at an uppermost position therein; air is supplied into the chamber 41 through an air pipe line 43 located in a middle position therein; and discharge is performed through an exhaust pipe line 44 located in a lowermost position therein. Voltage is applied to an electrode 45 through an electric wire 46 to generate plasma PM on the lower side in the chamber 41. Such a pipe as a glass tube, a rubber tube, or a synthetic resin tube is used as the helium pipe line 42, the air pipe line 43, and the exhaust pipe line 44.

Such a structure using the three pipes provides relatively a better efficiency. Since the helium having a low concentration tends to stay in an upper portion of the chamber 41, it is possible to reduce the consumption of the relatively expensive helium. When an application to a human body is taken into account, the interface portion of the chamber 41, i.e., a contact portion located in the lowest position thereof, is made to have a soft structure using a silicone resin or the like so that air tightness is also maintained.

[Surgical Instruments]

There is a method to perform sterilization by drawing a vacuum and generating the plasma. In implementing such a method, an enhanced sterilization effect is expected when an acidic solution is applied. However, the pressure should be kept at a saturated vapor pressure of water or higher.

[Liquid Sterilization]

In each embodiment, sterilization is performed by bringing the plasma PM into contact with a liquid having a adjusted pH value.

When liquid sterilization is performed, the liquid is treated to become acid, and then discharges made available at a low cost such as spark discharges, arc discharges, or impulse discharges are performed. Through this process, an enhanced liquid sterilization performance is expected. This type of sterilization method is applicable to sewage treatment or the like.

[pH Adjustment by Carbonic Acid Gas]

The carbonic acid gas (carbon dioxide) is harmless to human body. Therefore, it is possible to perform neutralization treatment on a liquid, which has been subjected to a pH adjustment process, by using the carbonic acid gas dissolved in a liquid and merely leaving the liquid as is.

Usually, distilled water turns into an equilibrium state when the carbonic acid gas in the air dissolves thereinto, and maintains a pH value of approximately 5.6. However, it is possible to temporarily lower the pH value of the solution by actively dissolving the carbonic acid gas thereinto.

It is also possible to maintain the concentration of carbonate ions in the solution at a high level by generating the plasma under an atmosphere of a high carbonic acid gas concentration (a few percent to a few dozen percent of the carbonic acid gas concentration). In this case, it is not necessary to use a pressurized container because the partial pressure of the carbonic acid gas can be simply raised.

When the pH value is lowered by the carbonic acid gas, the pH value of the liquid that has been subjected to the sterilization process rises by itself to a pH value of 5.6 by allowing the liquid to make contact with the air. This method provides an advantage in that an object that has been sterilized in the liquid does not require a cleaning process again because chemical agents will never stay even after drying.

[pH Adjustment Method]

The form of a chemical agent for adjusting the pH is not particularly important. For example, if it is solid such as citric acid, it may be charged into the liquid as is and dissolved. Alternatively, it is also possible to add such a solution that has been prepared by adjusting the pH. Further, it is also possible to use a gas such as the carbonic acid gas which can dissolve in the water and function to lower the pH, and it is possible to lower the pH by actively dissolving the chemical agent or placing the liquid in the high concentration gas atmosphere.

If the object to be sterilized is not a liquid (or in a liquid), the pH value on the surface of the object is adjusted by applying or spraying a liquid having a adjusted pH value onto the surface.

When the acidic liquid is sprayed, spraying can be divided and performed in multiple times so as to prevent the acidic liquid from evaporating. When the object is made contact with the plasma PM in the chamber, the acidic liquid is supplied by spraying in a form of droplets while the plasma PM is generated. Additional spraying is performed as required while the plasma PM is generated.

Although an acidic liquid having a adjusted pH value is used in each embodiment, it is also possible to generate the plasma PM to perform sterilization and, at the same time, increase the pH of the liquid by decomposing the acidic substances.

For example, it can be arranged to increase the pH value to an appropriate value, e.g., 5.0 or higher when a liquid having a pH value of 3.0 is used, sterilization is performed by emitting the plasma PM for a predetermined period of time, and the sterilization is completed as the predetermined period has elapsed. In this way, by the time the sterilization is completed, the liquid has turned almost neutral and can be disposed of as is.

[LF Plasma Jet]

A description will be given of the LF plasma jet that is used throughout the present embodiment.

Figure 19:
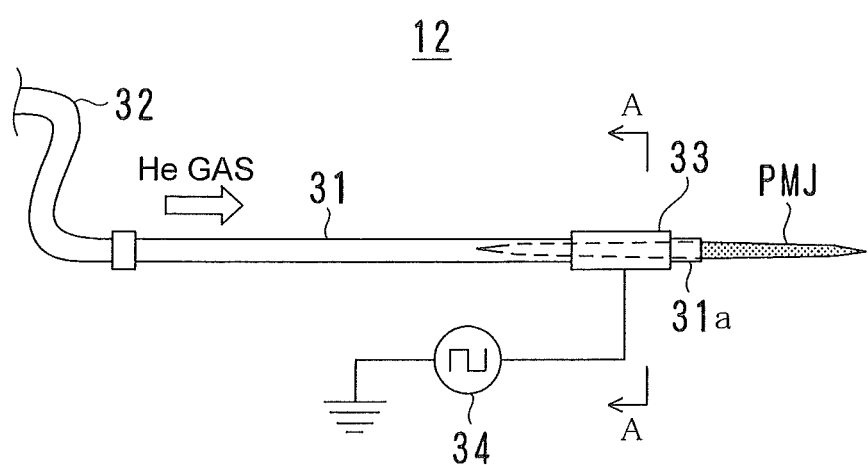
FIG. 19 is a front view of the plasma generation device for generating an LF plasma jet.
Figure 20:
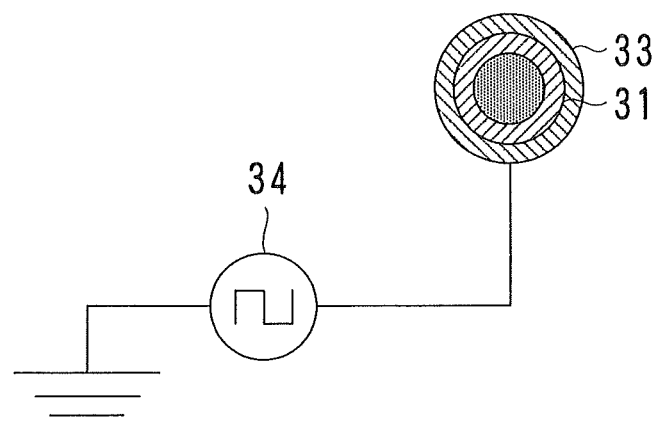
FIG. 20 is an enlarged sectional view of the plasma generation device taken along line A-A in FIG. 19.

In FIGS. 19 and 20, a plasma generation device 12 is configured of a gas supply pipe 31, a gas tube 32, a high-potential electrode 33, a voltage applying device 34, and so on.

The gas supply pipe 31 is formed of a dielectric such as a quartz pipe or a plastic tube and has a rear end thereof to which the gas tube 32 is connected. For example, helium (He) gas is supplied from an unillustrated medium gas source. The helium gas that has passed through a bore of the gas supply pipe 31 is jetted out from a jet port 31a to constitute a gas stream generating portion for forming a gas stream of a medium gas. A pipe having, for example, an inner diameter of 50 μm to 50 mm can be used as the gas supply pipe 31.

A coaxial single high-potential electrode 33 for generating plasma is provided on an outer circumference of an end portion on a side of the jet port 31a of the gas supply pipe 31. A voltage applying device 34 is connected to the high-potential electrode 33 to which a positive voltage in a form of pulse train having a predetermined frequency is applied. The voltage value to be applied by the voltage applying device 34 is set, for example, at 10 kV, and the frequency is set, for example, at about 10 kHz. With this arrangement, a non-equilibrium plasma jet PMJ that extends in an elongated shape from the jet port 31a is generated. This plasma jet PMJ is the LF plasma jet.

Thus, as represented by a broken line in FIG. 19, a phenomenon is observed in which the plasma jet PMJ generated only by a single high-potential electrode extends in both upstream and downstream directions of the medium gas stream from the high-potential electrode 33. Therefore, this discharge is not considered as a phenomenon in which the plasma generated around the high-potential electrode bursts out to the atmosphere by a helium gas stream but as a discharge phenomenon that occurs in a cylindrical space limited in a medium by a helium gas stream. That is, on the upstream and downstream sides of the medium gas stream with respect to the high-potential electrode 33, a partial discharge occurs between the high-potential electrode 33 and the ground potential far away from the high-potential electrode, and the discharge is the plasma limited in a medium that is produced only in the medium gas stream. Accordingly, in the plasma generation device 12, a short-circuit discharge does not occur between the electrodes. As a result, in both the upstream portion and the downstream portion of the high-potential electrode 33 (that is, outside of the high-potential electrode 33), plasma with a large aspect ratio is generated.

In order to generate a plasma stream limited in a medium only by partial discharge, the gas supply pipe 31 and the gas tube 32 function as a gas stream generating portion that generates a medium gas flux, and the high-potential electrode 33 and the voltage applying device 34 function as an electric field forming portion that forms an electric field corresponding to each medium gas stream.

It is also possible to provide an on-off valve that allows or prohibits passage of the helium gas in a junction portion between the gas supply pipe 31 and the gas tube 32 or in other portions. In addition, as described previously, it is also possible to provide a branch-off pipe line or a passage changeover valve to the gas supply pipe 31 in order to supply a plurality of types of fluids to the object by using the gas supply pipe 31.

Figure 21:
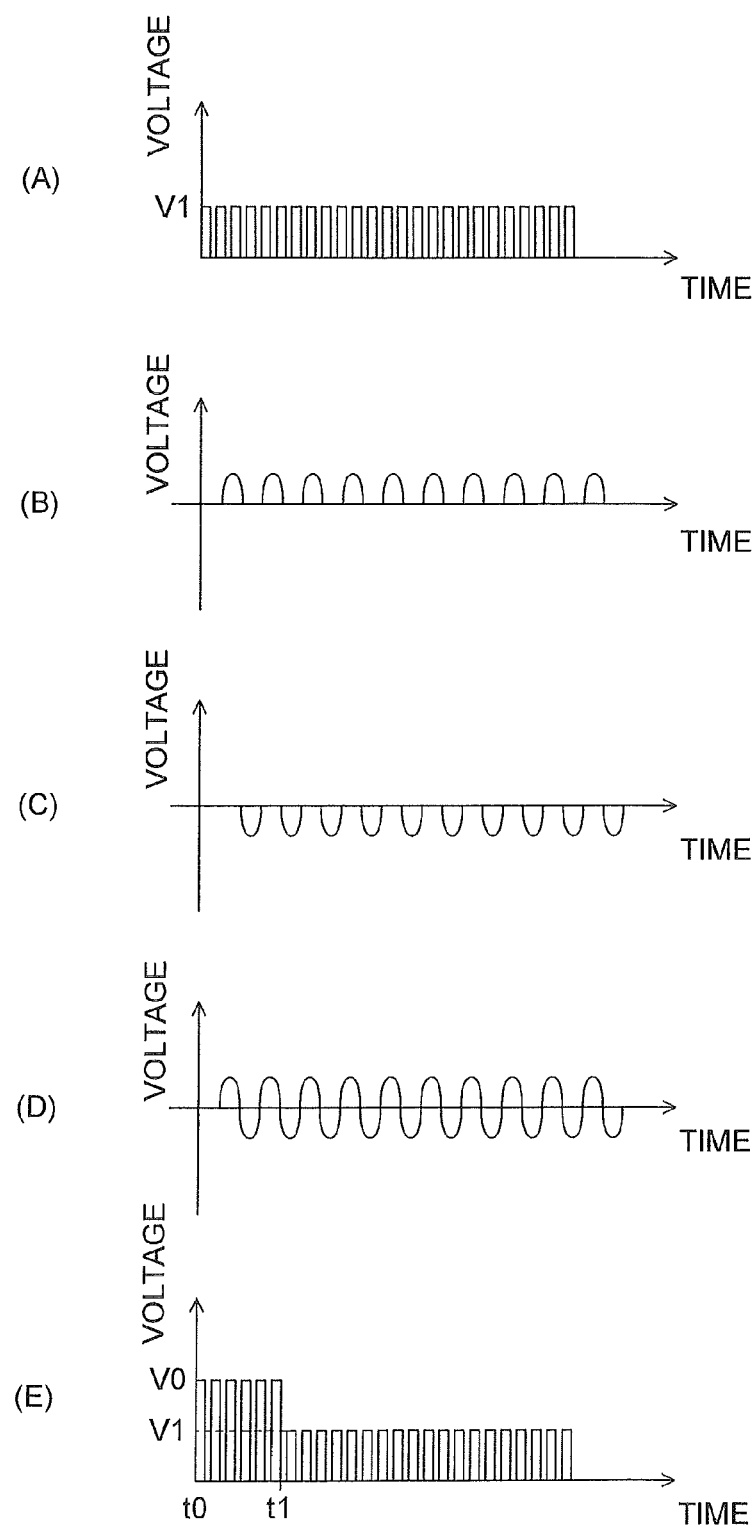
FIG. 21 is a diagram illustrating examples of voltage waveforms applied to an electrode.

The voltage applying device 34 applies a positive voltage in a form of pulse train having a predetermined frequency to the high-potential electrode 33. The voltage applying device 34 outputs, for example, a voltage having a waveform as illustrated in FIG. 21. If a voltage alternating in time is applied, plasma is likely to be generated by the alternating component in the voltage, particularly in the case of dielectric barrier discharge, since plasma is ignited via a capacitor of glass. Specifically, a voltage having a frequency of about 10 kHz can be used. However, it is sometimes a case in which glow-type atmospheric plasma may be obtained even with a voltage having a low frequency of about 60 Hz.

Although helium gas is preferred as a medium gas, another gas may also be used as long as conditions are set appropriately. For example, a mixed gas of argon and ketone also can be used. Further, various processes can be performed by supplying vapor of a chemical agent such as a monomer, or an aerosol such as sprayed mist or fine particles.

The LF plasma jet is a thermally non-equilibrium low-temperature plasma, which can be emitted to a base material such as thin nylon without causing any damage thereto but has energy sufficient for effecting a surface treatment, ozone generation, and a plasma polymerization.

It is also possible to provide a plurality of the high-potential electrodes 33 arranged for a single medium gas flow. By providing an arrangement for generating only a partial discharge, an increase in power consumption resulted from short-circuit discharges can be suppressed, and energy conversion efficiency can be improved, as compared with a conventional coaxial bi-electrode system. Furthermore, it is possible to eliminate an electrode on the ground side whose contribution to the generation of a plasma jet is small and therefore simplify the device. Even with a single high-potential electrode, it is easy to start the generation of the plasma jet PMJ.

Furthermore, according to a method for generating plasma in a space region limited in a medium by a medium gas flux, any medium gas flux is ionized to become plasma stably by causing only a partial discharge. The ignition of plasma can be realized on a wide scale of about 50 μm to 50 mm, and an increase in an aperture size is also possible in principle, using the above procedure.

According to the plasma generation device 12, only a high voltage in a form of pulse train is applied to the high-potential electrode 33 connected to the gas supply pipe 31 through which the medium gas flows, whereby a partial discharge is allowed to occur along the medium gas stream diffused from the gas supply pipe 31 to the atmosphere, which can generate a plasma stream. An example of configuring various conditions for the generation of a plasma stream is described hereinafter.

Medium gas: helium gas
Inner diameter of a quartz pipe: 3 mm
Flow rate of medium gas: several liters/minute.
Voltage applied to the high-potential electrode 33: 10 kV
Frequency of the applied voltage: 10 kHz
Furthermore, even using an electrode, e.g., width of 2 mm and length of 50 mm, having no plane closed in a rotation angle direction with respect to a medium gas flux, i.e., electrode covering only a part, plasma can be generated by partial discharge.

The LF plasma jet has two characteristics: "generation of a gas flux in the atmosphere" and "partial discharge in the vicinity of a high-potential electrode". Although discharge is allowed to occur by applying a periodic high voltage, plasma parameters can be controlled not only by the applied voltage but also by the applied frequency. In addition to these, the parameters of plasma to be generated can be also controlled by controlling the waveform (polarity) of a high voltage to be applied.

FIG. 21(B) illustrates a voltage waveform when only a positive high voltage is applied. FIG. 21(C) illustrates a voltage waveform when only a negative high voltage is applied. FIG. 21(D) illustrates a voltage waveform when positive and negative high voltages are applied alternately. In each case, discharge in a pulse form occurs at a moment when the applied voltage exceeds a predetermined absolute value that varies between the positive and negative voltages. For example, in the case of using a power source producing a voltage with a frequency of 10 kHz, one period is 100 μsec, and the discharge in the pulse form is observed within a few microseconds from the start.

The polarity of the high voltage that is being applied determines the densities and temperature distribution of ions, electrons, metastable atoms, and the like which are all generated from the plasma, and the plasma itself. Positive corona discharge occurs in the case of a positive voltage, and negative corona discharge occurs in the case of a negative voltage. The positive corona discharge and the negative corona discharge have different physical discharge mechanisms, so that the plasma production state varies. Thus, using the plasma while individual polarities are controlled makes it possible to control the effect of plasma on an object which is exposed to the plasma. On the other hand, in the case of FIG. 21(D), discharges of both the polarities occur. To be specific, in individual time regions in which the positive and negative high voltages rise respectively, the positive and negative corona discharges are generated in turn.

By controlling the applied waveforms of positive and negative high voltages in combination and thereby generating the plasma jets with different parameters, it is expected that selective promotion of chemical reactions can be performed.

It is desired that the voltage applying device 34 be configured so as to change the peak value of an applied voltage at a time of the ignition of plasma and the peak value of an applied voltage at a time of maintaining generation of plasma, as shown in FIG. 21(E). More specifically, for igniting the plasma jet PMJ, a high peak voltage of V0 is supplied from times t0 to t1, and a reduced peak voltage V1 is supplied after the time t1. The voltage V0 has a level sufficient for igniting a plasma jet PMJ, and the voltage V1 is a level required for maintaining the generation of a plasma jet PMJ. Although a high voltage is required for the ignition of a plasma jet PMJ, once a plasma jet is generated, the generation of the plasma jet PMJ can be maintained at a voltage lower than that required at a time of the ignition. Therefore, power consumption can be reduced by decreasing the applied voltage.

Furthermore, the high-potential electrode 33 is not always required to be provided coaxially on the outer circumferential surface of the gas supply pipe 31. The LF plasma jet can be generated even with an electrode attached to a part of the outer circumferential surface or inner circumferential surface of the gas supply pipe 31. More specifically, it is preferred that an electrode be attached to the inner surface or the outer surface of a member made of a dielectric for forming a medium gas stream, and that the dielectric and the electrode be integrally structured. When an electrode is attached to the inner surface of a member made of a dielectric, medium gas comes into contact with both the dielectric and the electrode.

Furthermore, the medium gas does not necessarily form a stream. This means that it is also possible to configure a plasma generation device so as to generate plasma from a medium gas mass. In this case, an electric field forming portion that forms an electric field in a medium gas mass is provided. If the medium gas mass has an elongated shape, an electric field is formed so as to cause partial discharges from the electric field forming portion toward both directions in the longitudinal direction of the medium gas mass. The medium gas mass may be arranged in such a manner that the medium gas is sealed in a tube provided with an electrode. Even in this case, the electrode may be provided either on the inner surface or the outer surface of the tube.

Alternatively, a needle may be fitted to the vicinity of the nozzle aperture for the j et and used as an electrode. In addition, when the plasma PM is generated in the liquid LQ, the plasma PM can be generated while the electrolysis of a liquid is performed at the same time by applying, to the electrode provided in the liquid LQ, a voltage resulted from superimposing a voltage required for generation of the plasma PM on a DC voltage required for performing electrolysis.

[Advantage of the Sterilization Method According to this Embodiment]

Sterilization is performed by exposing microorganisms to plasma in the gas phase according to the conventional sterilization by plasma. However, according to the sterilization in the liquid, it is difficult for active species of the plasma to penetrate into the liquid, resulting in an extremely low sterilization effect. Against this kind of problem, according to each embodiment described above, it is possible to significantly increase the microbiocidal activity by merely adjusting the pH value without involving use of particular chemical agents.

The embodiments provide significantly high practicality because, particularly, it is not necessary to exhaust gas for arranging a vacuum environment as conventionally required, but the atmospheric pressure serves for the purpose.

For example, each embodiment is expected to be applied not only to the sterilization of the medical equipment immediately before the surgical operation but also as a surgical tool for disinfecting human body. In surgical operations, complete sterilization of human organs is practically impossible, and overall sterilization is performed by such measures as administrating antibiotics. In contrast, since the sterilization performed by emitting the plasma jet works only on a part exposed to air, it is possible to perform sterilization in an appropriate area.

As described above, the sterilization of a liquid using the chamber can not be applied in a conventional method, whereas, in this embodiment, it becomes possible.

Finally, in each embodiment described above, the configurations of all or part of the plasma generation devices 12, 12B, 12E, and 12F, the container YK, the liquid LQ, the gelatin sheet 21, the sterilization apparatuses 1 and 1B, and other elements, shapes, dimensions, quantities, materials, voltage waveforms, periods, temperatures, types of gasses, and so on can be arbitrarily modified in various ways within the spirit of the present invention.

What is claimed is:

1. A method for sterilizing microorganisms present in a liquid or on a surface thereof, comprising:
    a first step of preadjusting the liquid to have a pH value of 4.8 or lower;
    a second step of generating plasma in a vicinity of or in a manner to make contact with the liquid whose pH value is adjusted to become 4.8 or lower in the first step; and
    a third step of supplying, through the plasma generated, the liquid whose pH value is adjusted to become 4.8 or lower in the first step with superoxide anion radicals ($O_2^-$.), reacting the superoxide anion radicals ($O_2^-$.) with protons ($H^+$) in the liquid, increasing a concentration of hydroperoxy radicals (HOO.) in the liquid, and sterilizing the microorganisms present in the liquid or on the surface thereof.

2. The method according to claim 1, wherein the plasma is generated in an atmosphere containing nitrogen gas.

3. The method according to claim 2, wherein the plasma is generated in air.

4. The method according to claim 3, wherein the pH value is 4.5 or lower.

5. The method according to claim 2, wherein the pH value is 4.5 or lower.

6. The method according to claim 5, wherein the pH value is 2 or higher but 3.5 or lower.

7. The method according to claim 1, wherein the pH value is 4.5 or lower.

\* \* \* \* \*